(12) United States Patent
Ogura et al.

(10) Patent No.: US 10,589,077 B2
(45) Date of Patent: Mar. 17, 2020

(54) MICRONEEDLE DEVICE SYSTEM

(71) Applicant: HISAMITSU PHARMACEUTICAL CO., INC., Tosu-shi, Saga (JP)

(72) Inventors: Makoto Ogura, Tsukuba (JP); Naoki Yamamoto, Tsukuba (JP); Takashi Kumon, Tsukuba (JP)

(73) Assignee: HISAMITSU PHARMACEUTICAL CO., INC., Tosu-shi, Saga (JP)

( * ) Notice: Subject to any disclaimer, the term of this patent is extended or adjusted under 35 U.S.C. 154(b) by 0 days.

(21) Appl. No.: 15/532,836

(22) PCT Filed: Dec. 4, 2015

(86) PCT No.: PCT/JP2015/084193
§ 371 (c)(1),
(2) Date: Jun. 2, 2017

(87) PCT Pub. No.: WO2016/088886
PCT Pub. Date: Jun. 9, 2016

(65) Prior Publication Data
US 2017/0333690 A1    Nov. 23, 2017

(30) Foreign Application Priority Data

Dec. 5, 2014 (JP) ................. 2014-247191

(51) Int. Cl.
*A61M 37/00*    (2006.01)

(52) U.S. Cl.
CPC ........ *A61M 37/0015* (2013.01); *A61M 37/00* (2013.01); *A61M 2037/0023* (2013.01)

(58) Field of Classification Search
CPC .................. A61M 37/0015; A61M 2037/0023
See application file for complete search history.

(56) References Cited

U.S. PATENT DOCUMENTS 6,537,264 B1    3/2003   Cormier et al.
2003/0199810 A1  10/2003  Trautman et al.
(Continued)

FOREIGN PATENT DOCUMENTS

| CN | 101076367 A | 11/2007 |
| CN | 101330941 A | 12/2008 |

(Continued)

OTHER PUBLICATIONS

International Search Report for PCT/JP2015/084193, dated Jan. 19, 2016 (PCT/ISA/210).
(Continued)

*Primary Examiner* — Amber R Stiles
(74) *Attorney, Agent, or Firm* — Sughrue Mion, PLLC

(57) ABSTRACT

A microneedle device system includes a microneedle device having a sheet-like microneedle having a sheet in which one surface is a skin contact surface and the other surface is a rear surface, and in which a plurality of microneedles are formed substantially along a surface of the sheet, and in which the microneedles in the skin piercing region are raised from the skin contact surface so as to be capable of piercing skin if the sheet is bent in a thickness direction, an adhesive layer that is disposed on the sheet-like microneedle, and a liner that is attached to the adhesive layer so as to be releasable therefrom, and an auxiliary tool having a bending portion which bends the microneedle device in the thickness direction, and on which the microneedle device is mounted so as to be movable along the bending portion.

2 Claims, 18 Drawing Sheets

(56) References Cited

U.S. PATENT DOCUMENTS

| | | |
|---|---|---|
| 2003/0211619 A1 | 11/2003 | Olson et al. |
| 2004/0087992 A1 | 5/2004 | Gartstein et al. |
| 2004/0265365 A1 | 12/2004 | Daddona et al. |
| 2005/0031676 A1 | 2/2005 | Wong et al. |
| 2005/0112135 A1 | 5/2005 | Cormier et al. |
| 2005/0245845 A1 | 11/2005 | Roe et al. |
| 2006/0149297 A1 | 7/2006 | Sherman et al. |
| 2007/0161964 A1 | 7/2007 | Yuzhakov |
| 2007/0293816 A1 | 12/2007 | Chan et al. |
| 2008/0108959 A1 | 5/2008 | Jung et al. |
| 2008/0125743 A1* | 5/2008 | Yuzhakov ......... A61M 37/0015 604/506 |
| 2008/0269685 A1 | 10/2008 | Singh et al. |
| 2010/0028390 A1 | 2/2010 | Cleary et al. |
| 2010/0130940 A1 | 5/2010 | Yuzhakov |
| 2010/0305473 A1 | 12/2010 | Yuzhakov |
| 2011/0034860 A1 | 2/2011 | Melsheimer |
| 2013/0331792 A1 | 12/2013 | Karp et al. |
| 2015/0157840 A1 | 6/2015 | Kominami et al. |

FOREIGN PATENT DOCUMENTS

| | | |
|---|---|---|
| CN | 101912288 A | 12/2010 |
| EP | 1 360 935 A1 | 11/2003 |
| GB | 2 448 493 A | 10/2008 |
| JP | 2005-503210 A | 2/2005 |
| JP | 2005-118428 A | 5/2005 |
| JP | 2006-345984 A | 12/2006 |
| JP | 2007-501070 A | 1/2007 |
| JP | 2007-518468 A | 7/2007 |
| JP | 2007-521090 A | 8/2007 |
| JP | 2007-535388 A | 12/2007 |
| JP | 2009-501066 A | 1/2009 |
| JP | 2012-90795 A | 5/2012 |
| JP | 2014-217520 A | 11/2014 |
| WO | 03/024518 A2 | 3/2003 |
| WO | 2005/004729 A1 | 1/2005 |
| WO | 2005/016440 A1 | 2/2005 |
| WO | 2005/051455 A2 | 6/2005 |
| WO | 2005/075016 A1 | 8/2005 |
| WO | 2005/107596 A2 | 11/2005 |
| WO | 2007/127811 A2 | 11/2007 |
| WO | 2008/010681 A1 | 1/2008 |
| WO | 2013/187392 A1 | 12/2013 |
| WO | 2014/003002 A1 | 1/2014 |
| WO | WO 2014058746 A1 * | 4/2014 ........ A61M 37/0015 |
| WO | 2014/126101 A1 | 8/2014 |

OTHER PUBLICATIONS

Extended European Search Report dated Jun. 22, 2018 issued by the European Patent Office in counterpart application No. 15866287.4.
Office Action dated May 31, 2019 in Chinese Patent Application No. 201580065024.8 with translation of Search Report only.
Communication dated Jul. 23, 2019, from the Japanese Patent Office in counterpart Application No. 2016-562700.

* cited by examiner

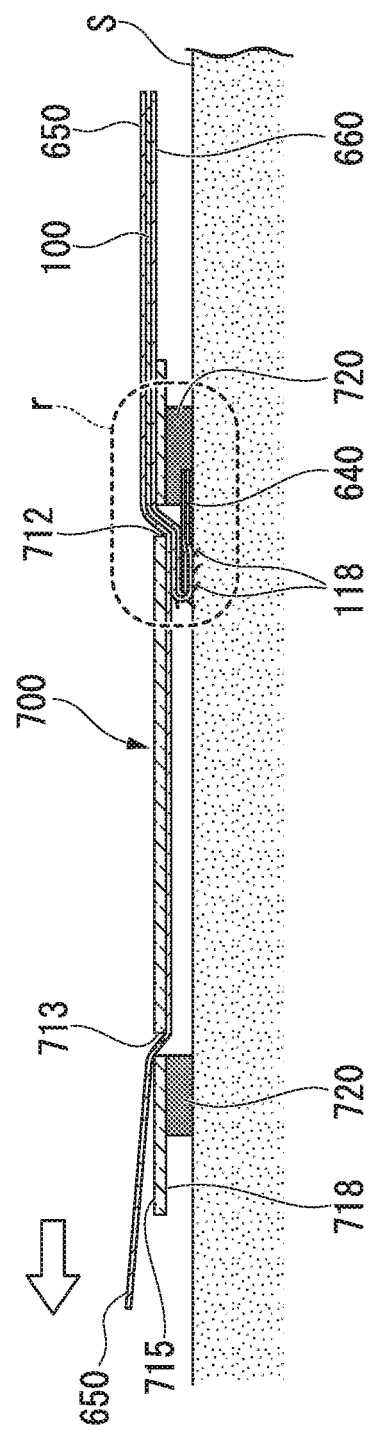

MICRONEEDLE DEVICE SYSTEM

CROSS REFERENCE TO RELATED APPLICATIONS

This application is a National Stage of International Application No. PCT/JP2015/084193 filed Dec. 4, 2015, claiming priority based on Japanese Patent Application No. 2014-247191, filed Dec. 5, 2014, the contents of all of which are incorporated herein by reference in their entirety.

TECHNICAL FIELD

The present invention relates to a microneedle device system. Priority is claimed on Japanese Patent Application No. 2014-247191, filed on Dec. 5, 2014, the content of which is incorporated herein by reference.

BACKGROUND ART

As one means for administering a drug via the skin, a microneedle is known. For example, Patent Literature 1 discloses a microneedle sheet that includes a plurality of microneedles formed in a sheet substantially along a principal surface of the sheet. In the microneedle sheet, the sheet is bent so as to raise the microneedles from the principal surface, and the raised microneedles pierce the skin.

A microneedle device including this sheet-like microneedle is also known. For example, Patent Literature 1 discloses a microneedle device in which the above-described sheet-like microneedle is fixed to an affixing surface of a base material which comes into contact with the skin when the microneedle device is applied to the skin so that the sheet-like microneedle is protected by a release film.

CITATION LIST

Patent Literature

[Patent Literature 1] PCT International Publication No. WO2013/187392

SUMMARY OF INVENTION

Technical Problem

However, according to the microneedle device disclosed in Patent Literature 1, one surface of the sheet-like microneedle is entirely fixed to the affixing surface of the base material. Therefore, there is room for improvement in a raised state of the microneedle when the sheet-like microneedle is bent in a thickness direction.

Therefore, the present invention aims to provide a microneedle device system which includes a sheet-like microneedle so as to improve a raised state of a microneedle.

Solution to Problem

The present invention is as follows.

(1) A microneedle device system which includes a microneedle device having a sheet-like microneedle having a sheet in which one surface is a skin contact surface and the other surface is a rear surface and whose one portion is a skin piercing region, in which a plurality of microneedles are formed substantially along a surface of the sheet, and in which the microneedles in the skin piercing region are raised from the skin contact surface so as to be capable of piecing the skin if the sheet is bent in a thickness direction, an adhesive layer that is disposed on the sheet-like microneedle, and a liner that is attached to the adhesive layer so as to be releasable therefrom and an auxiliary tool which has having a bending portion for bending the microneedle device in the thickness direction, and on which the microneedle device is mounted so as to be movable along the bending portion.

(2) The microneedle device system described in (1), in which the adhesive layer is disposed on a site excluding the rear surface of the skin piercing region of the sheet.

Advantageous Effects of Invention

According to the present invention, it is possible to provide a microneedle device system which includes a sheet-like microneedle so as to improve a raised state of a microneedle.

BRIEF DESCRIPTION OF DRAWINGS

FIG. 16A is a sectional view illustrating an embodiment of the microneedle device system fixed to the skin.

DESCRIPTION OF EMBODIMENTS

Figure 1:
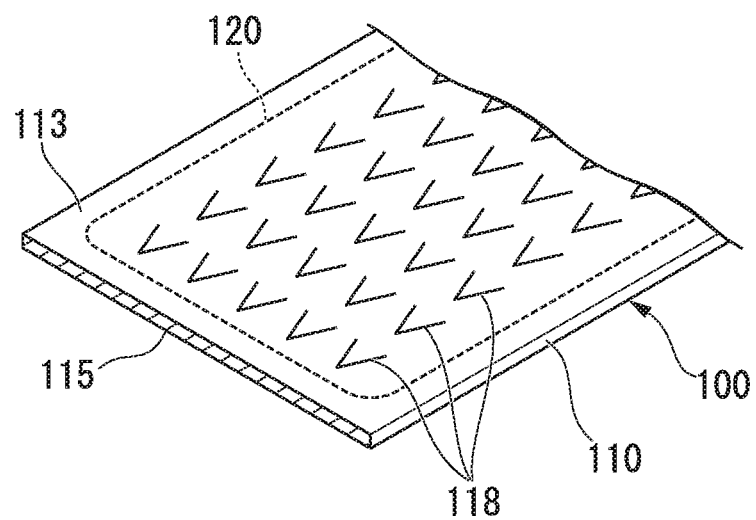
FIG. 1 is a perspective view illustrating an embodiment of a sheet-like microneedle.

Hereinafter, as the case may be, embodiments according to the present invention will be described with reference to the drawings. The same reference numerals will be given to the same or equivalent elements in the description of the drawings, and redundant description will be omitted.

According to an embodiment of the present invention, a microneedle device system, including a microneedle device having a sheet-like microneedle having a sheet in which one surface is a skin contact surface and the other surface is a rear surface and whose one portion is a skin piercing region, in which a plurality of microneedles are formed substantially along a surface of the sheet, and in which the microneedles in the skin piercing region are raised from the skin contact surface so as to be capable of piercing the skin if the sheet is bent in a thickness direction, an adhesive layer that is disposed on the sheet-like microneedle, and a liner that is attached to the adhesive layer so as to be releasable therefrom, and an auxiliary tool having a bending portion which bends the microneedle device in the thickness direction, and on which the microneedle device is mounted so as to be movable along the bending portion is provided.

In the present specification, the skin piercing region is a region on the sheet-like microneedle, and refers to a region where the microneedle for piercing the skin is actually present.

<Sheet-Like Microneedle>

First, the sheet-like microneedle will be described. FIG. 1 is a perspective view illustrating an embodiment of the sheet-like microneedle. A sheet-like microneedle 100 includes a sheet 110 in which one surface s a skin contact surface 113 and the other surface is a rear surface 115. The sheet 110 has a plurality of microneedles 118 formed substantially along a surface of the sheet 110.

The microneedles 118 are disposed with each other so as to align in each of a longitudinal direction and a width direction of the sheet 110. Each distal end of all of the microneedles 118 faces one end (forward direction in FIG. 1) of the sheet.

A material of the sheet-like microneedle 110 and the microneedle 118 is not particularly limited. For example, the material includes metal such as stainless steel, titanium, nickel-titanium alloy, tantalum, cobalt-chromium alloy, and magnesium alloy; biodegradable resins such as polylactic acid (PLA), glycolic acid (PGA), lactic acid-glycolic acid copolymer (PLGA), and polycaprolactone (PCL); synthetic resins such as polyethylene terephthalate (PET) and nylon; polysaccharides such as pullulan, hyaluronic acid, chondroitin sulfate; polyamino acids such as polylysine and polyglutamic acid; water-soluble polymers of synthetic polymers such as polyvinyl alcohol (PVA) and polyvinylpyrrolidone (PVP); and ceramics. These materials may be used alone or in combination of two or more. It is preferable that the material of the microneedle 118 be biocompatible. In the present specification, the term "biocompatible" refers to a property of the material which can be safely used without impairing a function of a living body or a component derived from the living body when the material is in contact with the living body or the living body-derived component. Specifically, the property includes antithrombogenicity to blood, low adsorption to proteins, non-adhesion and non-inflammatory properties to the living body, non-toxicity to cells, and non-irritability to living tissues.

For example, the microneedle 118 can be formed by means of etching. In a case where the sheet 110 is metal, the microneedle 118 can be formed by dissolving the sheet 110 with an etching agent solution. In addition, in a case where the sheet 110 is not metal, the microneedle 118 can be formed by punching the sheet 110 with a laser or the like, for example.

The microneedle 118 illustrated in FIG. 1 has a triangular shape. However, a shape of the microneedle is not particularly limited as long as the microneedle can pierce the skin. In manufacturing the sheet-like microneedle 100, it is not necessary to raise the microneedle 118 from the skin contact surface 113 of the sheet 110. Therefore, the sheet-like microneedle 100 can be easily and inexpensively manufactured.

A dimension of the sheet-like microneedle 100 is not particularly limited. For example, a thickness of the sheet-like microneedle 100 may be 5 to 1000 µm. Alternatively, for example, the thickness may be 10 to 300 µm. In addition, for example, a length in a longitudinal direction of the sheet-like microneedle 100 may be 0.1 to 50 cm. Alternatively, for example, the length may be 1 to 20 cm. For example, a width of the sheet-like microneedle 100 may be 0.1 to 60 cm. Alternatively, for example, the width may be 1 to 30 cm. The length and the width of the sheet-like microneedle 100 may be adjusted in view of a drug dose, for example. The length and the width of the sheet-like microneedle 100 may be adjusted in view of a size of the living body, for example.

A parameter relating to the microneedle 118 is not particularly limited. Specifically, a height of the microneedle 118 may be 10 to 10000 µm. Alternatively, for example, the height may be 100 to 1000 µm. In addition, for example, the density of the microneedle 118 may be 0.05 to 10,000/cm². Alternatively, for example, the density may be 1 to 5,000/cm².

If the sheet-like microneedle 100 is bent in a thickness direction thereof, the microneedle 118 in the skin piercing region 120 is raised from the skin contact surface 113, and the raised microneedle 118 pierces the skin.

<Microneedle Device>

Subsequently, embodiments of the mkroneedle device will be described. However, the microneedle device can be modified in various ways without being limited to the following embodiments.

First Embodiment

Figure 2A:
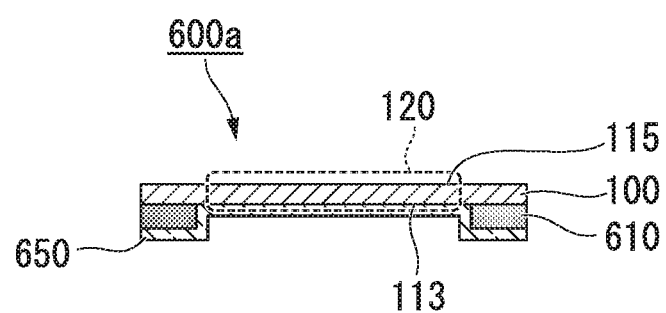
FIG. 2A is a sectional view illustrating an embodiment of a microneedle device.
Figure 2B:
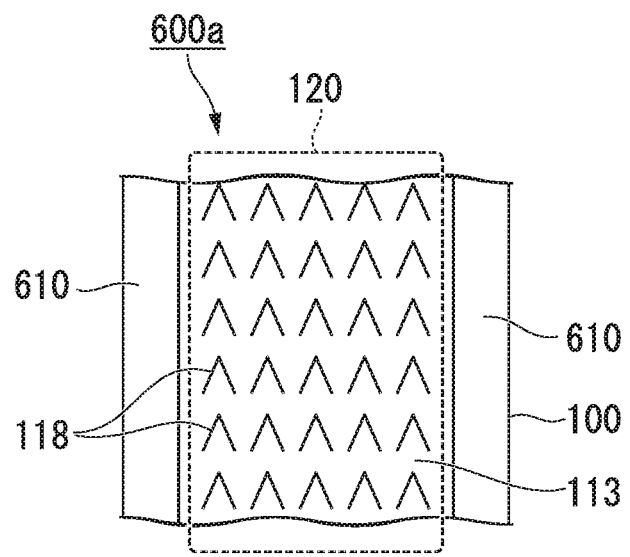
FIG. 2B is a plan view of the microneedle device illustrated in FIG. 2A.
Figure 2C:
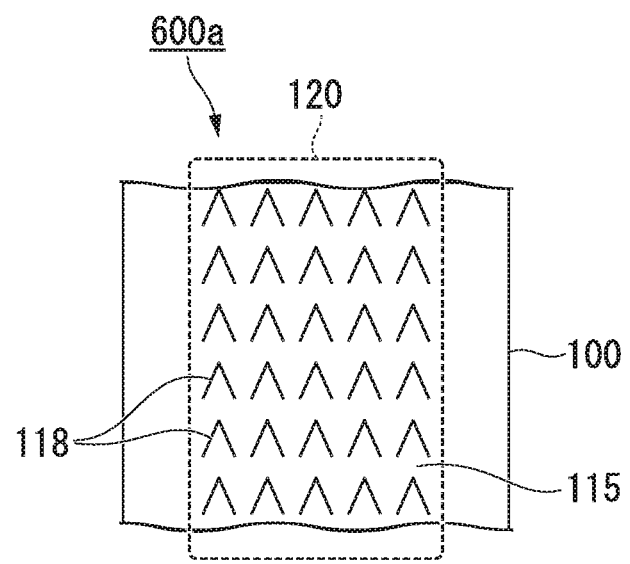
FIG. 2C is a plan view of the microneedle device illustrated in FIG. 2A.

FIGS. 2A to 2C are sectional views illustrating a first embodiment of the microneedle device. FIG. 2A illustrates a cross section including a cross section in the width direction of the sheet-like microneedle 100 included in a microneedle device 600a.

The microneedle device 600a includes the sheet-like microneedle 100, and an adhesive layer 610 laminated on the skin contact surface 113 excluding the skin piercing region 120 of the sheet-like microneedle 100 (region excluding the skin piercing region 120 on the skin contact surface 113). The adhesive layer 610 has a function to fix the microneedle device 600a to the skin when the microneedle device 600a is applied to the skin. In addition, the adhesive layer 610 may contain a drug. In addition, the adhesive layer is not laminated on the skin piercing region 120 of the rear surface 115 of the sheet-like microneedle 100. Therefore, when the sheet-like microneedle 100 is bent in the thickness direction, a raised state of the microneedle 118 is satisfactory, and the microneedle 118 can efficiently pierce the skin.

In the present embodiment, a liner 650 is attached onto the skin contact surface 113 and the adhesive layer 610 on an outer surface of the microneedle device 600a. In the present specification, the outer surface of the microneedle device is a surface on both sides in the thickness direction of the sheet-like microneedle, and refers to a portion which is not a side surface of the sheet-like microneedle. The liner 650 has a function to protect the microneedle device 600a. Furthermore, as will be described later, the liner 650 on the skin contact surface 113 side also has a function to raise the microneedle 118 of the sheet-like microneedle 100. That is, the liner 650 on the skin contact surface 113 side is a liner for raising the microneedle.

FIGS. 2B and 2C illustrate plan views of the microneedle device 600a. FIG. 2B illustrates a plan view when the liner 650 released from the microneedle device 600a is viewed from the skin contact surface 113 side of the sheet-like microneedle 100. As illustrated in FIG. 2B, in the microneedle device 600a, the adhesive layer 610 is laminated on a region excluding the skin piercing region 120 of the skin contact surface 113 of the sheet-like microneedle 100 (region which does not overlap the skin piercing region 120). FIG. 2C is a plan view when the microneedle device 600a is viewed from the rear surface 115 side of the sheet-like microneedle 100.

(Adhesive Layer)

An adhesive base material configuring the adhesive layer is not particularly limited. The adhesive base material includes styrene-based block copolymer, natural rubber, polyisobutylene resin, polyisoprene resin, silicone resin, and (meth) acrylic acid ester copolymer.

The adhesive layer may contain a tackifier resin. The tackifier resin includes rosin derivatives (for example, rosin, glycerin ester of rosin, hydrogenated rosin, glycerin ester of hydrogenated rosin, or pentaerythritol ester of rosin), alicyclic saturated hydrocarbon resin (for example, ARKON P100, Arakawa Chemical Industries, Ltd.), aliphatic, hydrocarbon resin (for example, Quinton B170, Zeon Corporation), terpene resin (for example, Clearon P-125, Yasuhara Chemical Co., Ltd), and maleic acid resin. One type of the tackifier resin may be used alone. Alternatively, two or more types may be used in a mixture.

The adhesive layer may contain a plasticizer. The plasticizer includes petroleum oil (for example, paraffinic process oil, liquid paraffin, naphthenic process oil, or aromatic process oil), squalane, squalane, vegetable oil (for example, olive oil, camellia oil, castor oil, tall oil, or peanut oil), silicone oil, dibasic acid ester (for example, dibutyl phthalate or dioctyl phthalate), liquid rubber (for example, liquid polybutene or liquid isoprene rubber), liquid fatty acid esters (for example, isopropyl myristate, hexyl laurate, diethyl sebacate, or diisopropyl sebacate), diethylene glycol, polyethylene glycol, glycol salicylate, propylene glycol, dipropylene glycol, triacetin, triethyl citrate, and crotamiton. Among these materials, liquid paraffin, liquid polybutene, isopropyl myristate, diethyl sebacate, hexyl laurate are preferably used. In particular, it is preferable to use liquid polybutene, isopropyl myristate, and liquid paraffin. One type of the plasticizer may be used alone. Alternatively, two or more types may be used in a mixture.

The adhesive layer may contain an absorption promoter. The absorption promoter may be any one of compounds whose absorption-promoting action in the skin is recognized. For example, the absorption promoter includes saturated or unsaturated fatty acid having 6 to 20 carbon atoms, saturated or unsaturated fatty alcohol having 2 to 10 carbon atoms, esters of saturated or unsaturated fatty acid having 6 to 20 carbon atoms, amides of saturated or unsaturated fatty acid having 6 to 20 carbon atoms, ethers, aromatic organic acid, aromatic alcohol, aromatic organic acid ester or ether (the above-described materials may be either saturated or unsaturated, and may be cyclic or linear branched). Furthermore, the absorption promoter includes lactic acid esters, acetic acid esters, monoterpene compounds, sesquiterpene compounds, azone, azone derivatives, pyrrothiodecane, glycerin fatty acid esters, propylene glycol fatty acid esters, sorbitan fatty acid esters (span type), polysorbate types (tween type), polyethylene glycol fatty acid esters, polyoxyethylene hydrogenated castor oil type (HCO type), polyoxyethylene alkyl ethers, sucrose fatty acid esters, and vegetable oils. Specifically, the absorption promoter includes caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric acid diethanolamide, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, l-menthol, borneol, d-limonene, isoeugenol, isoborneol, nerol, dl-camphor, glycerin monocaprylate, glycerin monocaprate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pyrrothiodecane, and olive oil. In particular, it is preferable to use oleic acid, oleyl alcohol, lauryl alcohol, isostearyl alcohol, lauric acid diethanolamide, glycerin monocaprylate, glycerin monocaprate, glycerol monooleate, sorbitan monolaurate, propylene glycol monolaurate, polyoxyethylene lauryl ether, and pyrothiodecane. One type of the absorption promoter may be used alone. Alternatively, two or more types may be used in a mixture.

For example, the adhesive layer can be produced by the following method. For example, the materials of the adhesive layer may be mixed with each other, thermally melted, applied to the released liner, and transferred to a predetermined position of the sheet-like microneedle. Alternatively, the materials of the adhesive layer may be mixed with each other, and dissolved in an organic solvent such as toluene, hexane, ethyl acetate, lower alcohol, or cyclohexane. After the materials are applied on the released liner, the organic solvent may be dried and removed at a predetermined temperature, the materials may be transferred to a predetermined position of the sheet-like microneedle.

The thickness of the adhesive layer is not particularly limited. For example, the thickness may be 20 to 1000 μm. Alternatively, for example, the thickness may be 50 to 500 μm.

(Drug)

In the microneedle device according to the present embodiment, the sheet-like microneedle may be used to deliver a drug. The drug may be contained in the adhesive layer, and may be contained in the material itself of the sheet-like microneedle. Alternatively, the drug may be loaded on a surface or a void of the sheet-like microneedle by means of application/printing, embedding, or laminating. Before or after the sheet-like microneedle is applied to the skin, the drug may be directly applied to an application site. Alternatively, a reservoir (drug containing portion) of the drug may be separately disposed. For example, a drug storage layer includes an adhesive layer 630 in a microneedle device 600f according to a sixth embodiment (to be described later).

The applicable drug using the microneedle device is not particularly limited. For example, the drug includes antibiotics, antifungal agents, antitumor agents, cardiotonic agents, therapeutic agents for arrhythmia, vasodilators, antihypertensive agents, diuretics, hypotensive diuretics, antihypertensive diuresis drugs for circulatory organs, antiplatelet drugs, hemostatic agents, antihyperlipidemic agents, antipyretic/analgesic/antiinflammatory agents, antirheumatic drugs, relaxants, antitussive expectorants, antiulcer agents, sedatives, antiepileptics, anti-inflammatory agents, antiallergic agents, therapeutic agents for diabetes, antituberculosis agents, hormonal agents, narcotic antagonists, bone resorption suppressants, angiogenesis inhibitors, and local anesthetics.

(Liner)

The material of the liner is not particularly limited. The material includes metal; polyester such as polyethylene terephthalate (PET); polyolefin such as ethylene vinyl acetate copolymer (EVA), polyurethane (PU), polyethylene (PE), and polypropylene (PP); resins such as polyether sulfone (PES), polycarbonate (PC), polystyrene (PS), Teflon (registered trademark), and (meth) acrylate resin; and elastomers. In the present specification, (meth) acrylic acid refers to methacrylic acid or acrylic acid.

For example, the surface of the liner may be subjected to release treatment by using release treatment agents such as silicone type release treatment agents, fluorine type elease treatment agents, long-chain alkyl type release treatment agents, fatty acid amide type release treatment agents, and silica powder.

(Support)

As will be described later, the microneedle device may include a support. The material of the support is not particularly limited. The material includes metal; polyester such as polyethylene terephthalate (PET); polyolefinsuch as ethylene vinyl acetate copolymer (EVA), polyurethane (PU), polyethylene (PE), and polypropylene (PP); resins such as polyether sulfone (PES), polycarbonate (PC), polystyrene (PS), Teflon (registered trademark), and (meth) acrylate resin; and elastomers. In the present specification, (meth) acrylic acid refers to methacrylic acid or acrylic acid.

In the present specification, the liner is an easily releasable film, and the support is a film which cannot be released or is not supposed to be released. For example, whether or not the film is easily releasable depends on whether or not a film surface is subjected to release treatment.

Figure 3:
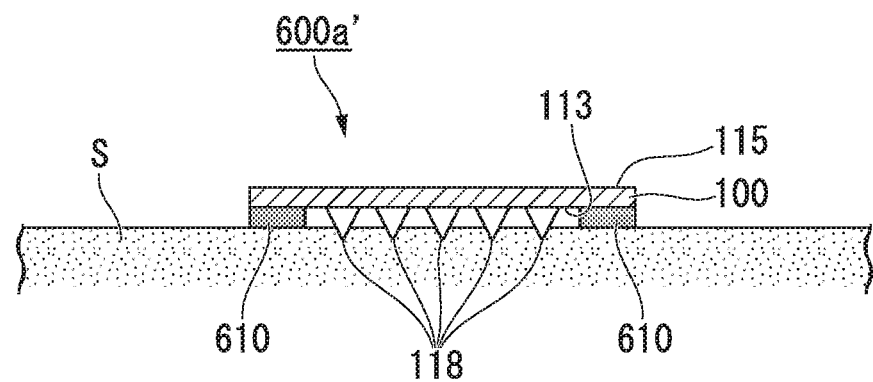
FIG. 3 is a sectional view illustrating a state where the microneedle device illustrated in FIG. 2A is applied to the skin.

FIG. 3 is a view illustrating a state where the microneedle device 600a is applied to the skin (the microneedle device 600a'). In the microneedle device 600a' applied to the skin, the liner 650 is released when the microneedle device 600a is applied to the skin S. In addition, the microneedle 118 is raised from the skin contact surface 113 of the sheet-like microneedle 100, and pierces the skin S. In addition, the adhesive layer 610 enables the microneedle device 600a' to be fixed onto the skin S.

Second Embodiment

Figure 4:
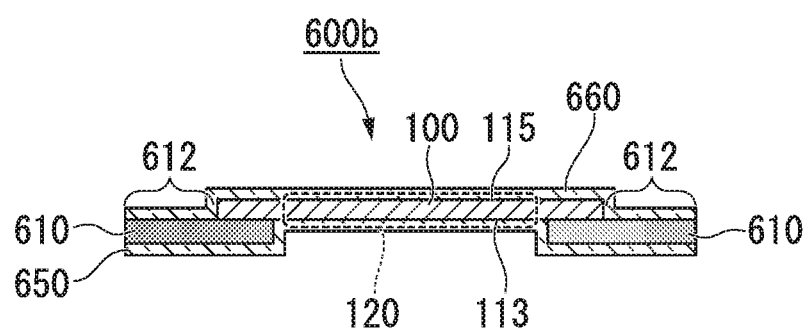
FIG. 4 is a sectional view illustrating an embodiment of the microneedle device.

FIG. 4 is a sectional view illustrating a second embodiment of the microneedle device. FIG. 4 illustrates a cross section including a cross section in the width direction of the sheet-like microneedle 100 included in a microneedle device 600b.

The microneedle device 600b includes the sheet-like microneedle 100 and the adhesive layer 610 laminated on the skin contact surface 113 excluding the skin piercing region 120 of the sheet-like microneedle 100 (region excluding the skin piercing region 120 on the skin contact surface 113). The adhesive layer 610 has a region 612 extending outward from the sheet-like microneedle 100 in plan view of the microneedle device 600b.

The adhesive layer 610 has a function to fix the microneedle device 600b to the skin when the microneedle device 600b is applied to the skin. In addition, the adhesive layer 610 may contain a drug. In addition, the adhesive layer is not laminated on the skin piercing region 120 of the rear surface 115 of the sheet-like microneedle 100. Therefore, when the sheet-like microneedle 100 is bent in the thickness direction, a raised state of the microneedle 118 is satisfactory, and the sheet-like microneedle 100 can efficiently pierce the skin.

In the present embodiment, the liner 650 is attached onto the skin contact surface 113 and the adhesivelayer 610 of the outer surface of the microneedle device 600b. The support 660 is disposed on the rear surface 115 of the sheet-like microneedle 100 which is the other outer surface and on the region 612 of the adhesive layer 610. The liner 650 and the support 660 have a function to protect the microneedle device 600b. Furthermore, as will be described later, the liner 650 on the skin contact surface 113 side also has a function to raise the microneedle 118 of the sheet-like microneedle 100. That is, the liner 650 on the skin contact surface 113 side is a liner used to raise the microneedle. The materials of the adhesive layer, the drug, the liner, and the support are the same as those described above.

Since the microneedle device according to the present embodiment has a simple structure, the microneedle device can be easily manufactured. In addition, the microneedle device according to the present embodiment includes the support 660. Accordingly, for example, when the sheet-like microneedle 100 is bent in the microneedle device system according to a third embodiment (to be described later), it is possible to prevent the adhesive layer 610 from being bonded and fixed to a cylindrical portion 100A of a member A or to prevent the adhesive layers 610 from being bonded and fixed to each other. The above-described advantageous effect of the support 660 in the microneedle device (to be described later) is common to those including the support 660.

Figure 5:
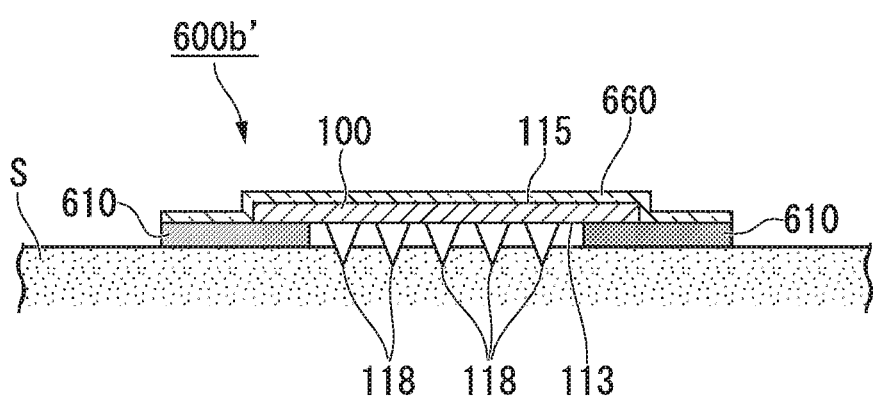
FIG. 5 is a sectional view illustrating a state where the microneedle device illustrated in FIG. 4 is applied to the skin.

FIG. 5 is a view illustrating a state where the microneedle device 600b is applied to the skin (microneedle device 600b'). In the microneedle device 600b' applied to the skin, the liner 650 on the skin contact surface 113 side is released when the microneedle device 600b is applied to the skin S, and the support 660 on the rear surface 115 side is left.

left support 660 can protect the microneedle device 600b'.

In addition, the microneedle 118 is raised from the skin contact surface 113 of the sheet-like microneedle 100, and pierces the skin S. In addition, the adhesive layer 610 enables the microneedle device 600b' to be fixed onto the skin S.

Third Embodiment

Figure 6:
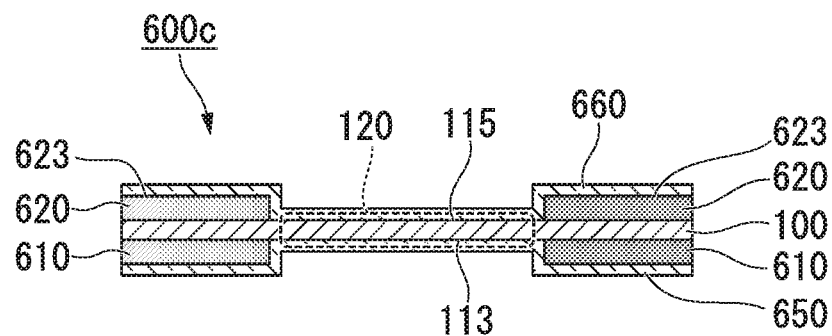
FIG. 6 is a sectional view illustrating an embodiment of the microneedle device.

FIG. 6 is a sectional illustrating the third embodiment of the microneedle device. FIG. 6 illustrates a cross section including a cross section in the width direction of the sheet-like microneedle 100 included in a microneedle device 600c.

The microneedle device 600c includes the sheet-like microneedle 100, the adhesive layer 610 laminated oil the skin contact surface 113 excluding the skin piercing region 120 of the sheet-like microneedle 100 (region excluding the skin piercing region 120 on the skin contact surface 113), and an adhesive layer 620 laminated on a portion of the rear surface 115 of the sheet-like microneedle 100 (region excluding the skin piercing region 120 on the rear surface 115). The adhesive layer 610 may contain a drug. In addition, the adhesive layer is not laminated on the skin piercing region 120 of the rear surface 115 of the sheet-like microneedle 100. Therefore, when the sheet-like microneedle 100 is bent in the thickness direction, a raised state of the microneedle 118 is satisfactory, and the sheet-like microneedle 100 can efficiently pierce the skin.

In the present embodiment, the liner 650 attached onto the skin contact surface 113 and the adhesive layer 610 of the outer surface of the microneedle device 600c. The support 660 is disposed on the rear surface 115 of the sheet-like microneedle 100 which is the other outer surface and on a surface 623 on a side opposite to the sheet-like microneedle 100 in the adhesive layer 620. The liner 650 and the support 660 have a function to protect the microneedle device 600c. Furthermore, as will be described later, the liner 650 on the skin contact surface 113 side also has a function to raise the microneedle 118 of the sheet-like microneedle 100. That is, the liner 650 on the skin contact surface 113 side is a liner used to raise the microneedle. The materials of the adhesive layer, the drug, the liner, and the support are the same as those described above.

Figure 7:
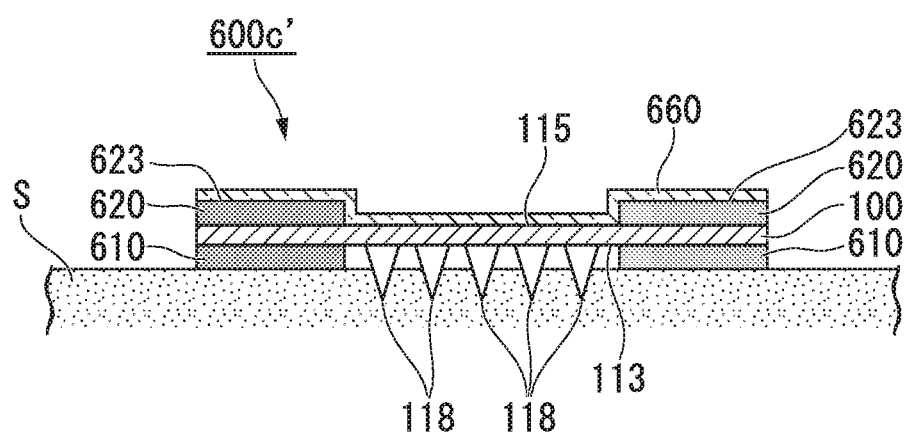
FIG. 7 is a sectional view illustrating a state where the microneedle device illustrated in FIG. 6 is applied to the skin.

FIG. 7 is a view illustrating a state where the microneedle device 600c is applied to the skin (microneedle device 600c'). In the microneedle device 600c' applied to the skin, when the microneedle device 600c is applied to the skin S, the liner 650 on the skin contact surface 113 side is released, and the support 660 on the rear surface 115 side is left.

The left support 660 can protect the microneedle device 600c'.

In addition, the microneedle 118 is raised from the skin contact surface 113 of the sheet-like microneedle 100, and pierces the skin S. In addition, the adhesive layer 610 enables the microneedle device 600c' to be fixed onto the skin S.

Fourth Embodiment

Figure 8:
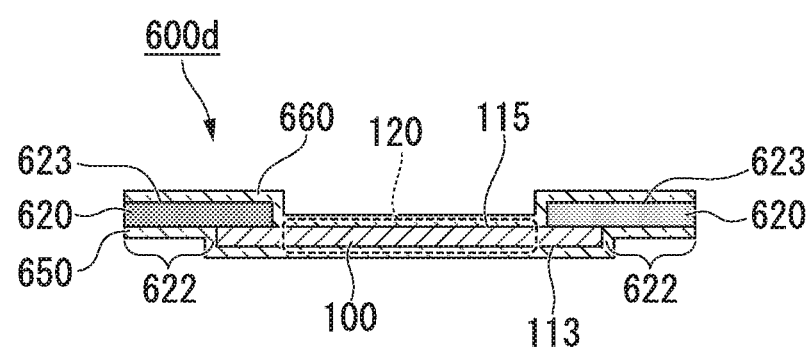
FIG. 8 is a sectional view illustrating an embodiment of the microneedle device.

FIG. 8 is a sectional view illustrating a fourth embodiment of the microneedle device. FIG. 8 illustrates a cross section including a cross section in the width direction of the sheet-like microneedle 100 included in a microneedle device 600d.

The microneedle device 600d includes the sheet-like microneedle 100 and the adhesive layer 620 laminated on a portion of the rear surface 115 of the sheet-like microneedle 100 (region excluding the skin piercing region 120 on the rear surface 115). The adhesive layer 620 has a region 622 extending outward from the sheet-like microneedle 100 in plan view of the microneedle device 600d. An adhesive force in this region enables the microneedle device to be fixed to the skin. The adhesive layer 620 may contain a drug.

In the present embodiment, the support 660 is disposed on the outer surface of the microneedle device 600d, that is, on the rear surface 115 of the sheet-like microneedle 100, and on the surface 623 on a side opposite to the sheet-like microneedle 100 in the adhesive layer 620. The liner 650 is attached onto the skin contact surface 113 and the region 622 of the adhesive layer 620.

The liner 650 and the support 660 have a function to protect the microneedle device 600d. Furthermore, as will be described later, the liner 650 on the skin contact surface 113 side also has a function to raise the microneedle 118 of the sheet-like microneedle 100.

That is, the liner 650 on the skin contact surface 113 side is a liner used to raise the microneedle. The materials of the adhesive layer, the drug, the liner, and the support are the same as those described above. Since the microneedle device according to the present embodiment has a simple structure, the microneedle device can be easily manufactured.

The adhesive layer is not laminated on the skin piercing region 120 on the rear surface 115 of the sheet-like microneedle 100 of the microneedle device 600d. Therefore, when the sheet-like microneedle 100 is bent in the thickness direction, a raised state of the microneedle 118 is satisfactory, and the sheet-like microneedle 100 can efficiently pierce the skin.

Figure 9:
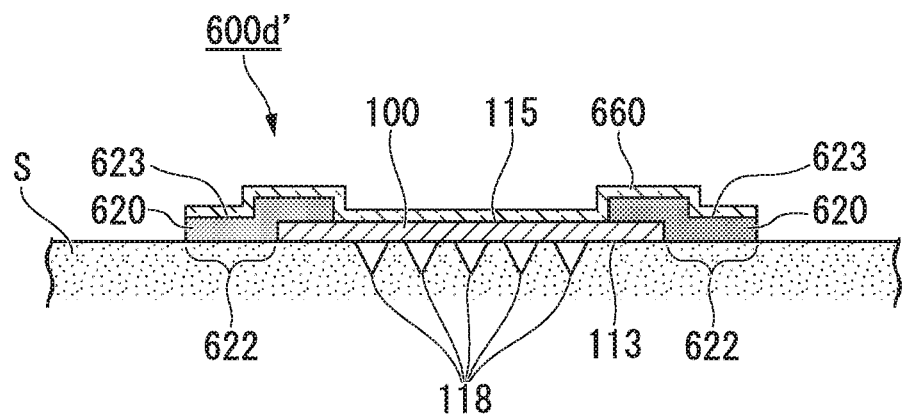
FIG. 9 is a sectional view illustrating a state where the microneedle device illustrated in FIG. 8 is applied to the skin.

FIG. 9 is a view illustrating a state where the microneedle device 600d is applied to the skin (microneedle device 600d'). In the microneedle device 600d' applied to the skin, when the microneedle device 600d is applied to the skin S, the liner 650 on the skin contact surface 113 side is released, and the support 660 on the rear surface 115 side is left.

The left support 660 can protect the microneedle device 600d'.

In addition, the microneedle 118 is raised from the skin contact surface 113 of the sheet-like microneedle 100, and pierces the skin S. In addition, the region 622 of the adhesive layer 620 enables the microneedle device 600d' to be fixed onto the skin S.

Fifth Embodiment

Figure 10:
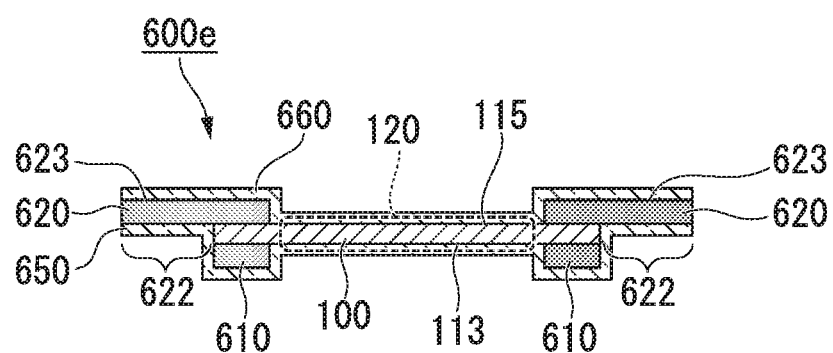
FIG. 10 is a sectional view illustrating an embodiment of the microneedle device.

FIG. 10 is a sectional view illustrating a fifth embodiment of the microneedle device. FIG. 10 illustrates a cross section including a cross section in the width direction of the sheet-like microneedle 100 included in a microneedle device 600e. The microneedle device according to the present embodiment is a combination of the microneedle devices according to the above-described second and fourth embodiments.

The microneedle device 600e includes the sheet-like microneedle 100, the adhesive layer 610 laminated on the skin contact surface 113 excluding the skin piercing region 120 of the sheet-like microneedle 100 (region excluding the skin piercing region 120 on the skin contact surface 113), and the adhesive layer 620 laminated on a portion of the rear surface 115 of the sheet-like microneedle 100 (region excluding the skin piercing region 120 on the rear surface 115). The adhesive layer 620 has the region 622 extending outward from the sheet-like microneedle 100. The adhesive layer 610 or the adhesive layer 620 may contain a drug.

In the present embodiment, the support 660 is disposed on the outer surface of the microneedle device 600e, that is, on the rear surface 115 of the sheet-like microneedle 100, and on the surface 623 on a side opposite to the sheet-like microneedle 100 in the adhesive layer 620. The liner 650 is attached onto the skin contact surface 113, the adhesive layer 610, and the region 622 of the adhesive layer 620. The liner 650 and the support 660 have a function to protect the microneedle device 600e. Furthermore, as will be described later, the liner 650 on the skin contact surface 113 side also has a function to raise the microneedle 118 of the sheet-like microneedle 100. That is, the liner 650 on the skin contact surface 113 side is a liner used to raise the microneedle. The materials of the adhesive layer, the drug, the liner, and the support are the same as those described above.

The adhesive layer is not laminated on the skin piercing region 120 on the rear surface 115 of the sheet-like microneedle 100 of the microneedle device 600e. Therefore, when the sheet-like microneedle 100 is bent in the thickness direction, a raised state of the microneedle 118 is satisfactory, and the sheet-like microneedle 100 can efficiently pierce the skin.

Figure 11:
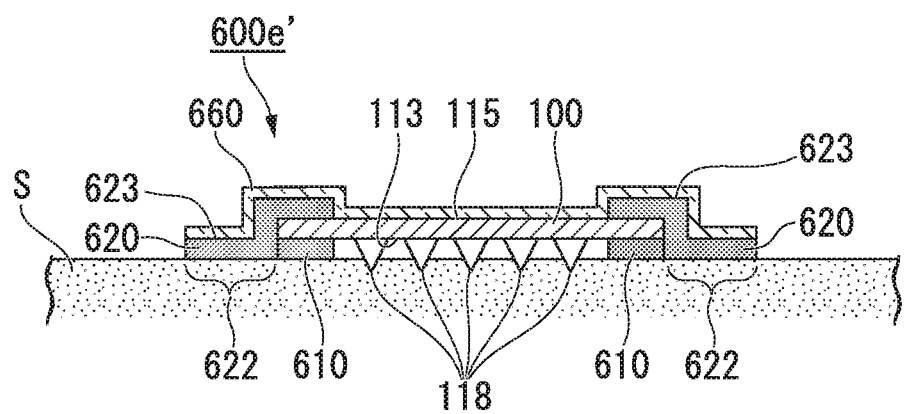
FIG. 11 is a sectional view illustrating a state where the microneedle device illustrated in FIG. 10 is applied to the skin.

FIG. 11 is a view illustrating a state where the microneedle device 600e is applied to the skin (microneedle device 600e'). In the microneedle device 600e' applied to the skin, when the microneedle device 600e is applied to the skin S, the liner 650 on the skin contact surface 113 side is released, and the support 660 on the rear surface 115 side is left. The left support 660 can protect the microneedle device 600e'. In addition, the microneedle 118 is raised from the skin contact surface 113 of the sheet-like microneedle 100, and pierces the skin S. In addition, the adhesive layer 610 and the region 622 of the adhesive layer 620 enable the microneedle device 600e' to be fixed onto the skin S.

In the microneedle device 600e', the microneedle device 600e' can be fixed onto the skin S by not only the adhesive layer 610 but also the region 622 of the adhesive layer 620. Accordingly, the microneedle device 600e' can be more firmly fixed.

Sixth Embodiment

Figure 12:
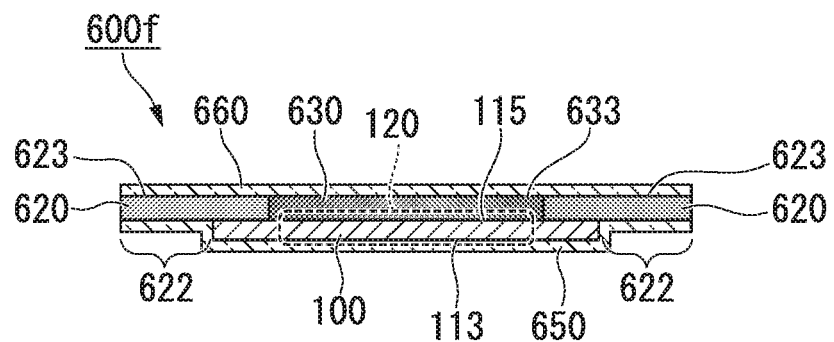
FIG. 12 is a sectional view illustrating an embodiment of the microneedle device.

FIG. 12 is a sectional view illustrating a sixth embodiment of the microneedle device. FIG. 12 illustrates a cross section including a cross section in the width direction of the sheet-like microneedle 100 included in a microneedle device 600f.

The microneedle device 600f includes the sheet-like microneedle 100, the adhesive layer 620 laminated on a portion of the rear surface 115 of the sheet-like microneedle 100 (region excluding the skin piercing region 120 on the rear surface 115), and an adhesive layer 630 laminated on a portion of the rear surface 115 of the sheet-like microneedle 100 (skin piercing region 120 on the rear surface 115).

The adhesive layer 620 has the region 622 extending outward from the sheet-like microneedle 100. An adhesive force in his region enables the microneedle device to be fixed to the skin. In addition, the adhesive force of the adhesive layer 630 is adjusted to be weak to such an extent that the adhesive force does not hinder a raised state of the microneedle 118. In addition, the adhesive layer 620 or the adhesive layer 630 may contain a drug.

In addition, in the present embodiment, the support 660 is disposed on the outer surface of the microneedle device 600f, that is, on the surface 623 on a side opposite to the sheet-like microneedle 100 in the adhesive layer 620, and on a surface 633 on a side opposite to the sheet-like microneedle 100 in the adhesive layer 630. The liner 650 is attached onto the skin contact surface 113 and the region 622 of the adhesive layer 620. The liner 650 and the support 660 have a function to protect the microneedle device 600f. Furthermore, as will be described later, the liner 650 on the skin contact surface 113 side also has a function to raise the microneedle 118 of the sheet-like microneedle 100. That is, the liner 650 on the skin contact surface 113 side is a liner used to raise the microneedle. The materials of the adhesive layer, the drug, the liner, and the support are the same as those described above.

Figure 13:
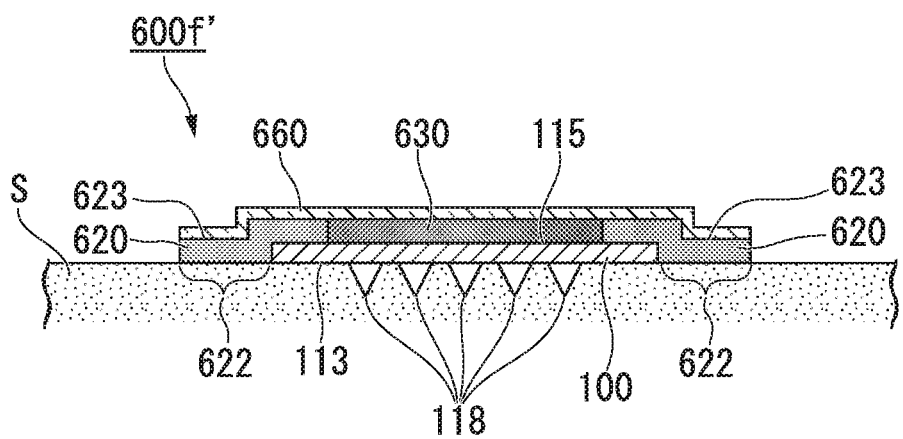
FIG. 13 is a sectional view illustrating a state where the microneedle device illustrated in FIG. 12 is applied to the skin.

FIG. 13 is a view illustrating a state where the microneedle device 600f is applied to the skin (microneedle device 600f'). In the microneedle device 600f' applied to the skin, when the microneedle device 600f is applied to the skin S, the liner 650 on the skin contact surface 113 side is released, and the support 660 on the rear surface 115 side is left. The left support 660 can protect the microneedle device 600f'. In addition, the microneedle 118 is raised from the skin contact surface 113 of the sheet-like microneedle 100, and pierces the skin S. In addition, the region 622 of the adhesive layer 620 enables the microneedle device 600f' to be fixed onto the skin S. In addition, in a case where the adhesive layer 630 contains a drug, the drug can be efficiently administered to a living body via the skin pierced by the microneedle 118.

Seventh Embodiment

Figure 21:
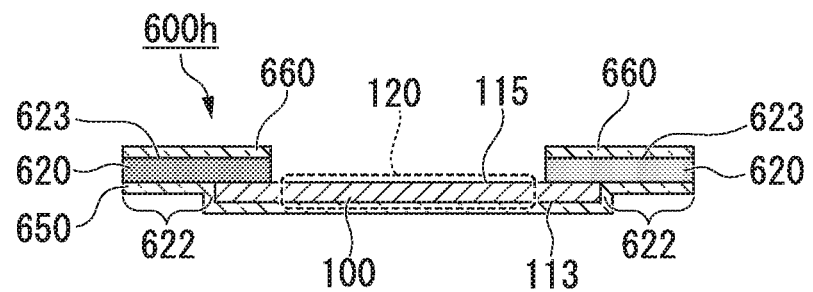
FIG. 21 is a sectional view illustrating an embodiment of the microneedle device.

FIG. 21 is a sectional view illustrating a structure of a microneedle device 600h. The microneedle device 600h does not have the support 660 in the skin piercing region 120 on the rear surface 115 of the above-described microneedle device 600d. That is, in the microneedle device 600h, the support 660 is disposed on the surface 623 of the adhesive layer 620. The materials of the adhesive layer, the drug, the liner, and the support are the same as those described above.

Figure 22:
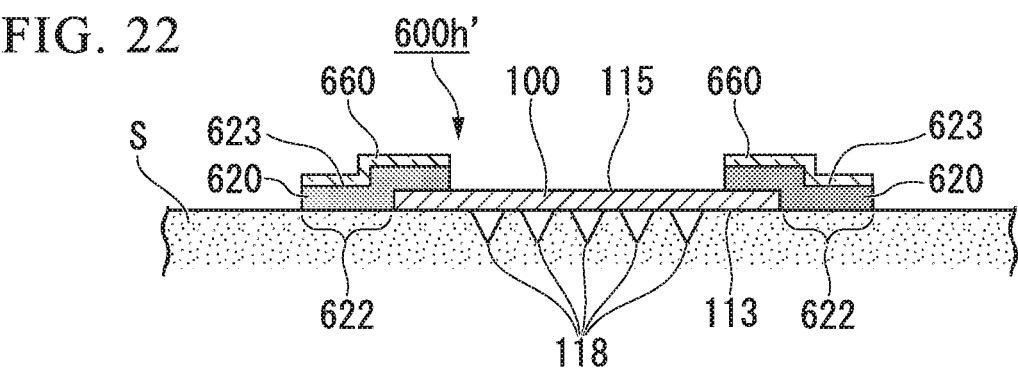
FIG. 22 is a sectional view illustrating a state where the microneedle device illustrated in FIG. 21 is applied to the skin.

FIG. 22 is a view illustrating a state where the microneedle device 600h is applied to the skin (microneedle device 600h'). In the microneedle device 600h' applied to the skin, when the microneedle device 600h is applied to the skin S, the liner 650 on the skin contact surface 113 side is released, and the support 660 on the surface 623 of the adhesive layer 620 is left. The left support 660 can protect the adhesive layer 620. In addition, the microneedle 118 is raised from the skin contact surface 113 of the sheet-like microneedle 100, and pierces the skin S. In addition, the region 622 of the adhesive layer 620 enables the microneedle device 600h' to be fixed onto the skin S.

The microneedle device 600h' does not have the support 660 in the skin region 120 of the rear surface 115. Accordingly, the drug can be efficiently administered to a living body from the rear surface 115 side in the skin piercing region 120.

Eighth Embodiment

Figure 23:
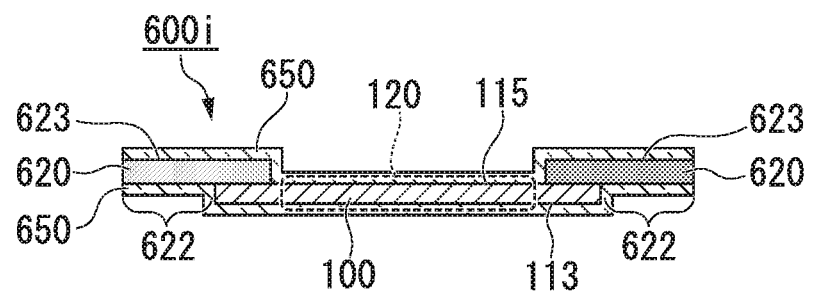
FIG. 23 is a sectional view illustrating an embodiment of the microneedle device.

FIG. 23 is a sectional view illustrating a structure of a microneedle device 600i. The microneedle device 600i has a structure in which the liner 650 is disposed instead of the support 660 in the above-described microneedle device 600d. That is, the liner 650 is disposed on the rear surface 115 of the sheet-like microneedle 100, and on the surface 623 of the adhesive layer 620. The liner 650 is also attached onto the skin contact surface 113 and the region 622 of the adhesive layer 620. The materials of the adhesive layer, the drug, the liner, and the support are the same as those described above.

Figure 24:
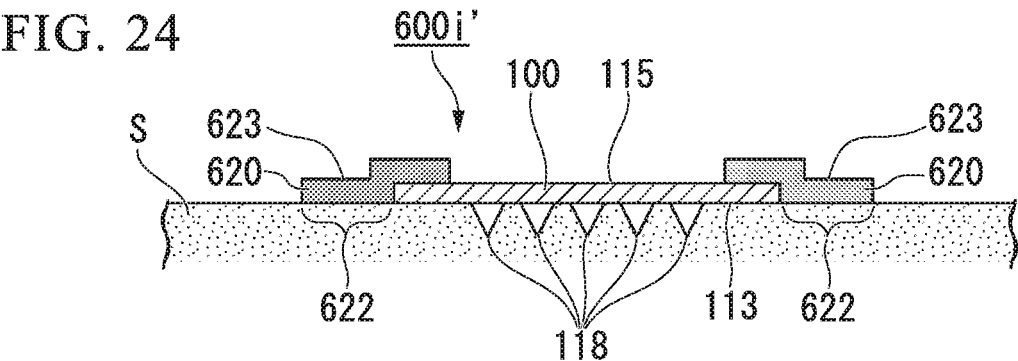
FIG. 24 is a sectional view illustrating a state where the microneedle device illustrated in FIG. 23 is applied to the skin.

FIG. 24 is a view illustrating a state where the microneedle device 600i is applied to the skin (microneedle device 600i'). In the microneedle device 600i' applied to the skin, when the microneedle device 600i is applied to the skin S, the liner 650 disposed on the rear surface 115 of the sheet-like microneedle 100 and on the surface 623 of the adhesive layer 620 and the liner 650 disposed on the skin contact surface 113 side are released, and the surface 623 of the adhesive layer 620 is exposed. In addition, the microneedle 118 is raised from the skin contact surface 113 of the sheet-like microneedle 100, and pierces the skin S. In addition, the region 622 of the adhesive layer 620 enables the microneedle device 600i' to be fixed onto the skin S.

The microneedle device 600i' does not have the support 660 in the skin piercing region 120 of the rear surface 115. Accordingly, the drug can be efficiently administered to a living body from the rear surface 115 side in the skin piercing region 120. In addition, for example, in a case where a drug-containing film is laminated on the rear surface 115 of the sheet-like microneedle 100, the drug-containing film can be fixed using the surface 623 of the adhesive layer 620.

Another Embodiment

The respective embodiments of the above-described microneedle device may be appropriately combined with each other. For example, similarly to the microneedle devices 600h and 600i, the microneedle devices 600b, 600c, and 600e may have a structure which does not partially or entirely have the support 660.

Microneedle Device System

First Embodiment

In an embodiment according to the present invention, a microneedle device system is provided, including a microneedle device having a sheet-like microneedle in which one surface s a skin contact surface and the other surface is a rear surface, in which a plurality of microneedles are formed substantially along a surface of a sheet whose one portion is a skin piercing region, and in which the microneedles in the skin piercing region are raised from the skin contact surface so as to be capable of piercing the skin if the sheet is bent in a thickness direction, an adhesive layer that is disposed on the sheet-like microneedle, and a liner that is attached to the adhesive layer so as to be releasable therefrom, and an auxiliary tool having a bending portion which bends the microneedle device in the thickness direction, and on which the microneedle device is mounted so as to be movable along the bending portion.

Figure 14:
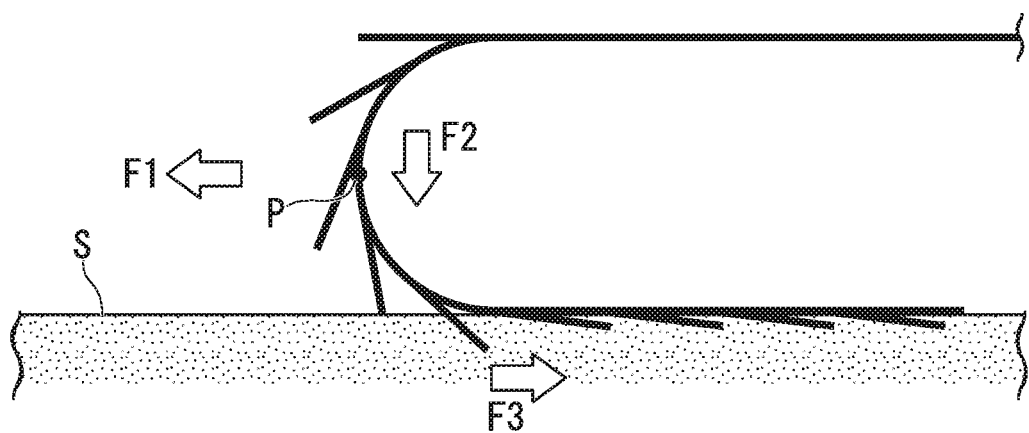
FIG. 14 is a sectional view illustrating a state where the microneedle pierces the skin.

First, a force and a direction thereof which are required when the microneedle pierces the skin will be described. FIG. 14 is a sectional view the longitudinal direction of the sheet-like microneedle 100 which illustrates a state where the microneedle 118 of the sheet-like microneedle 100 pierces the skin S. In order to cause the microneedle 118 to pierce the skin, as illustrated in FIG. 14, at least the following forces are required in a state where the sheet-like microneedle is bent in a thickness direction. The forces include a force F1 for moving a bending point P in a skin-piercing direction, a force F2 for creating a curvature to bend the sheet-like microneedle 100, and a force F3 for fixing a portion of the sheet-like microneedle 100 to the skin. The force F2 may be applied in a direction perpendicular to the principal surface of the sheet.

Furthermore, in order to achieve the piercing of the microneedle, a magnitude relationship of the forces F1 to F3 needs to be appropriate. Specifically, in order to move the bending point P in the skin-piercing direction by using the force F1, the force F3 needs to be always stronger than the force F1. In addition, in order for the microneedle 118 to pierce the skin and to have the curvature suitable for piercing, the force F2 needs to be greater than zero. That is, when two conditions of F1≤F3 and F2>0 are established at the same time, the microneedle 118 can continuously pierce the skin. In addition, if the force F2 is further strengthened, the microneedle 118 can more deeply pierce the skin. For example, in a case where the sheet-like microneedle 100 is fixed to the skin by using the adhesive layer having the width of 4 mm, the magnitude of the force F3 may be 24.7 N or greater.

Figure 15:
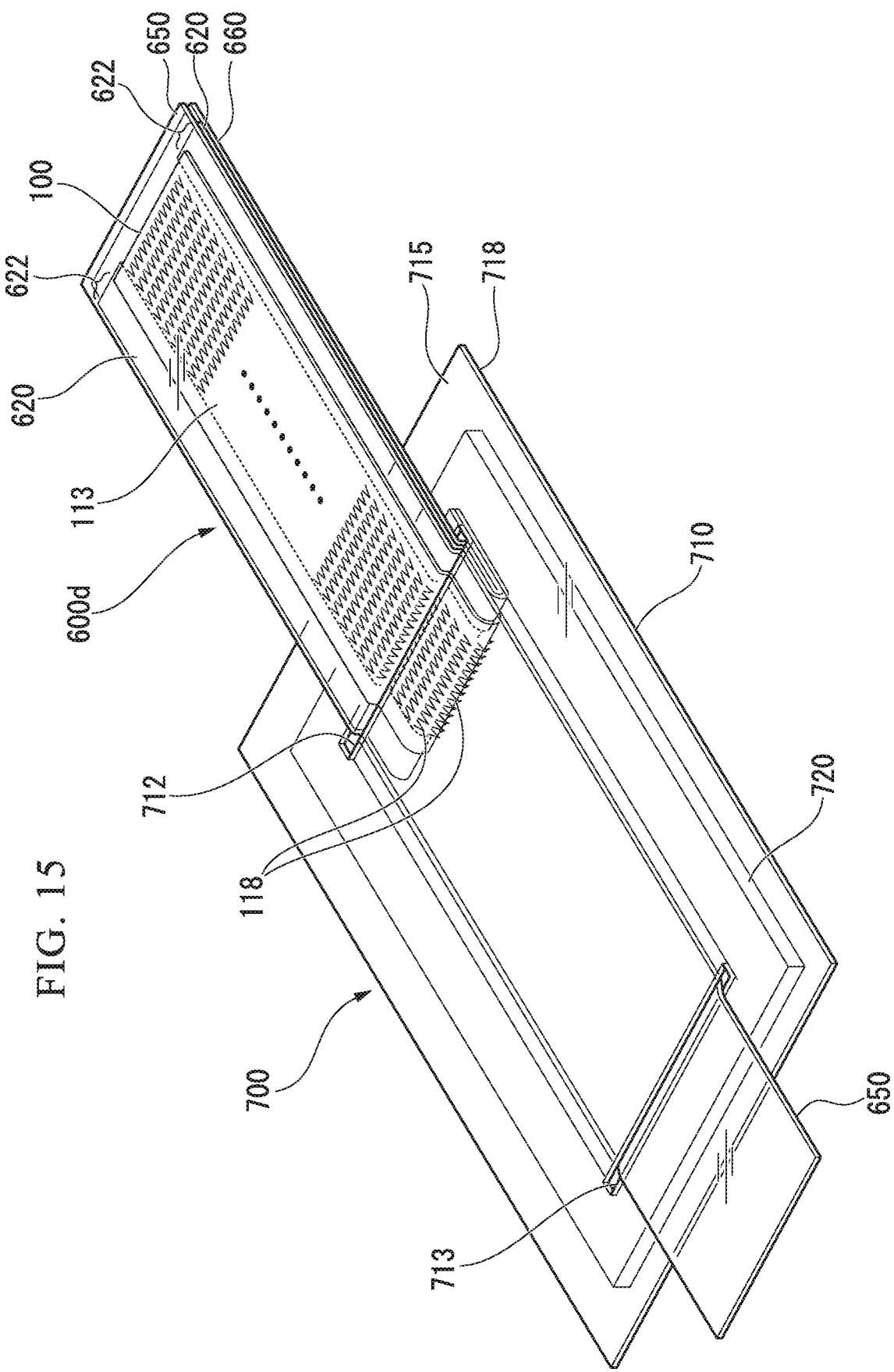
FIG. 15 is a perspective view illustrating an embodiment of a microneedle device system.

FIG. 15 is a perspective view illustrating an embodiment of the microneedle device system. Hereinafter, a process of piercing the skin by using the microneedle 118 of the microneedle device 600d of the above-described fourth embodiment will be described with reference to an auxiliary tool 700.

The microneedle device system according to the present embodiment includes the microneedle device 600d and the auxiliary tool 700. First, the auxiliary tool 700 will be described. As illustrated in FIG. 15, the auxiliary tool 700 includes a rectangular substrate 710, two slit-like through-holes 712 and 713 disposed on the substrate 710, and an adhesive layer 720 laminated on one surface 718 of the substrate 710. Hereinafter, a surface on a side opposite the surface 718 of the substrate 710 is referred to as a surface 715. In FIG. 15, since the substrate 710 is transparent, the adhesive layer 720 can be seen therethrough. In addition, since the liner 650 is also transparent, the sheet-like microneedle 100 can be seen therethrough. As will be described later, a portion on the through-hole 713 side from the through-hole 712 in the substrate 710 functions as a bending portion for bending the microneedle device 600d in the thickness direction.

In FIG. 15, the liner 650 attached to the outer surface on the skin contact surface 113 side is longer than the sheet-like microneedle 100 in the longitudinal direction, and a region in which the liner 650 is not in contact with the sheet-like microneedle 100 is present therein.

First, a user sets the microneedle device 600d in the auxiliary tool 700 by passing one end of the liner 650 through the through-hole 712 and the through-hole 713, and assembles the microneedle device system. More specifically, the user passes one end of the liner 650 attached to the outer surface on the skin contact surface 113 side from the surface 715 side of the through-hole 712 toward the surface 718 side. Furthermore, the user passes one end from the surface 718 side of the through-hole 713 toward the surface 715 side.

Through the above-described operation, the liner 650 is located on the surface 718 side between the through-hole 712 and the through-hole 713 as illustrated in FIG. 16A.

Subsequently, as illustrated in FIG. 15, the user bends the sheet-like microneedle 100 in the thickness direction on the surface 718 side between the through-hole 712 and the through-hole 713. While maintaining this state, the user bonds the auxiliary tool 700 to a drug application site by using the adhesive layer 720.

FIG. 16A is a sectional view in the longitudinal direction of the auxiliary tool 700 fixed onto the skin S by performing the above-described operation. As illustrated in FIG. 16A, the auxiliary tool 700 is fixed onto the skin S by the adhesive layer 720. The sheet-like microneedle 100 is caused to pass from the surface 715 side toward the surface 718 side through the through-hole 712, and is bent in the thickness direction on the skin S. Here, a portion on the through-hole 713 side from the through-hole 712 in the substrate 710 functions as a bending portion for bending the microneedle device 600d in the thickness direction.

Figure 16B:
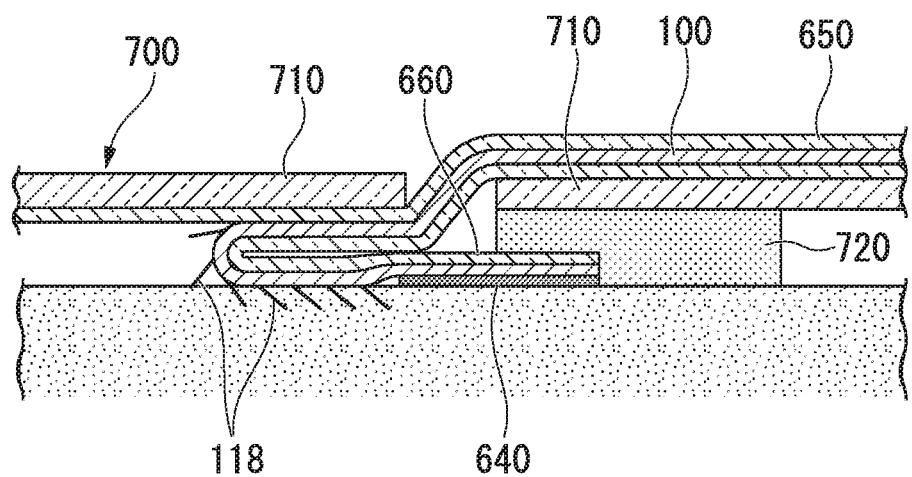
FIG. 16B is an enlarged view of a region r in FIG. 16A.

FIG. 16B is an enlarged view of a region r in FIG. 16A. As illustrated in FIG. 16B, according to the present embodiment, one end of the sheet-like microneedle 100 is fixed onto the skin S by the adhesive layer 640. In addition, one end of the sheet-like microneedle 100 may be further fixed onto the skin S by the adhesive layer 720.

Subsequently, the user pinches one end of the liner 650 and pulls one end in a direction indicated by an arrow in FIG. 16A, that is, in a direction away from one end fixed by the through-hole 712 and the adhesive layer 640. Through this operation, the sheet-like microneedle 100 is guided by the liner 650, passes through the through-hole 712, and enters a space between the skin S and the substrate 710 of the auxiliary tool 700.

Figure 17:
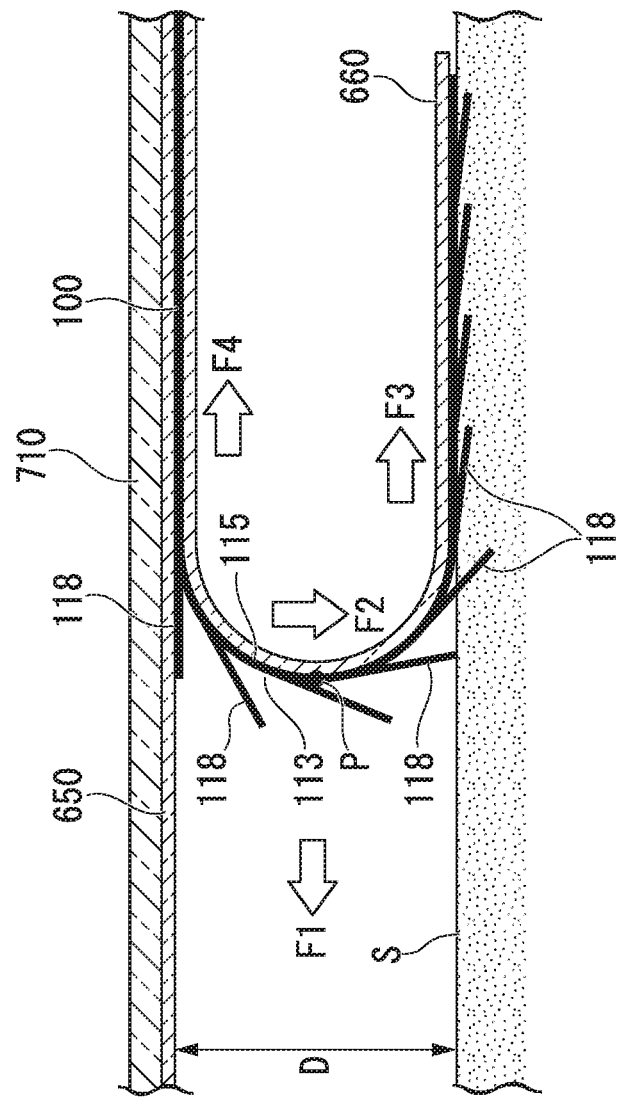
FIG. 17 is a sectional view illustrating a state where a sheet-like microneedle bent on the skin pierces the skin.

The sheet-like microneedle 100 is bent 180 degrees inside this space. Then, as illustrated in FIG. 17, the microneedle 118 located in the bent portion is raised from the skin contact surface 113, and the raised microneedle 118 pierces the skin S.

This process will be described in more detail. As illustrated FIG. 17, the force F2 is generated in a direction perpendicular to the skin S by limiting a distance D between the substrate 710 of the auxiliary tool 700 and the skin S. As a result, the microneedle 118 is raised from the sheet-like microneedle 100 folded by the force F2.

Here, a user pulls the liner 650 with the force F1. In this manner, a drag force F3 is generated by the region 622 of the adhesive layer 620 and the adhesive force between the adhesive layer 720 and the skin contact surface, and a drag force F4 is generated by the adhesive force between the region 622 of the adhesive layer 620 and the liner contact surface. As a result, the bending point P is continuously moved, and the microneedle 118 located at the folded position can pierce the skin. In this case, the maximum intensity of the force F3 needs to be greater than. the force F1, and the maximum intensity of the force F4 needs to be smaller than the force F1. The force F1 which contributes to the movement of the bending point P and the force F2 which contributes to raising the microneedle 118 are simultaneously generated. Accordingly, the microneedle 118 can pierce the skin. In FIG. 17, the adhesive layer 620 cannot be seen due to a position relationship of the illustrated cross section.

If the user pulls the liner 650 until the whole liner 650 is pulled out from the auxiliary tool 700, the whole sheet-like microneedle 100 pierces the skin S. In addition, at this time, the sheet-like microneedle 100 is fixed onto the skin S by the region 622 of the adhesive layer 620 in FIG. 15.

Thereafter, the user can release the auxiliary tool 700 from the skin S. In addition, in a case where the user wishes to pierce the skin barrier, the sheet-like microneedle 100 may be immediately released. Alternatively, in a case where the sheet-like microneedle 100 holds a drug, the sheet-like microneedle 100 may be continuously applied to the skin S over a predetermined period of time.

The microneedle device system according to the present embodiment has a configuration in which the liner 650 passes through the through-hole 713. Accordingly, it is easy to draw the liner 650 more accurately and straight. However, a modification example of the microneedle device system according to the present embodiment may adopt a configuration in which the through-hole 713 is not present. In this case, the liner 650 may be pulled in a direction away from the through-hole 712 through the surface 718 side of the substrate 710.

In addition, in the microneedle device system according to the above-described embodiment, the sheet-like microneedle 100 is firmly fixed onto the skin S by the adhesive layer 640 in addition to the adhesive layer 620. However, another modification example of the microneedle device system according to the present embodiment may adopt a configuration in which the adhesive layer 640 is not present.

Second Embodiment

Figure 18:
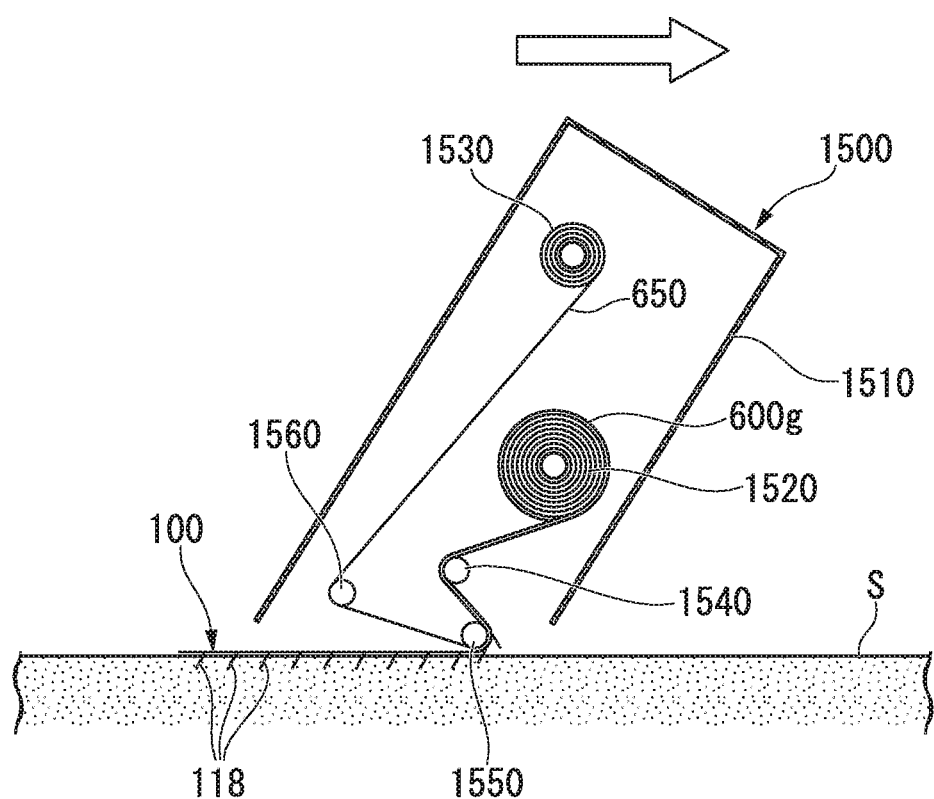
FIG. 18 is a sectional view illustrating an embodiment of the microneedle device system.

FIG. 18 a sectional view illustrating another embodiment of the microneedle device system. The microneedle device system according to the present embodiment includes an auxiliary tool 1500 and a microneedle device 600g wound in a roll shape. The microneedle device 600g includes a configuration in which the liner 650 is removed in the above-described microneedle device 600b described above, and furthermore in which the liner 650 instead of the support 660 is attached so as to be releasable therefrom.

The auxiliary tool 1500 includes a housing 1510, an attachment portion 1520 of the microneedle device, a bending portion 1550 for bending the microneedle device in the thickness direction, a liner-winding portion 1530, and guides 1540 and 1560.

The microneedle device 600g is mounted on the auxiliary tool 1500 so as to be movable along the bending portion 1550, thereby forming the microneedle device system.

As illustrated in FIG. 18, a user moves the microneedle device system in the arrow direction while pressing the microneedle device system against the skin S. Then, the microneedle device 600b moves along the bending portion 1550, and is bent in the thickness direction at the bending portion 1550. The microneedle 118 in the skin piercing region 120 of the sheet-like microneedle 100 is raised from the skin contact surface 113 of the sheet-like microneedle 100, and the raised microneedle 118 pierces the skin S. The sheet-like microneedle 100 is fixed onto the skin S by the adhesive layer 610. That is, according to the present embodiment, a force for moving the auxiliary tool 1500 corresponds to the above-described force F1. In addition, the liner 650 released from the microneedle device 600g is wound around the liner-winding portion 1530.

As described above, in the microneedle device 600g, the adhesive layer is not laminated on the skin piercing region 120 of the rear surface 115 of the sheet-like microneedle 100. Therefore, a raised state of the microneedle 118 is satisfactory.

In the microneedle device system according to the present embodiment, the microneedle device according to any embodiment can be used instead of the microneedle device 600g.

According to the microneedle device system of the present embodiment, it is possible to easily apply the microneedle device to the skin. In addition, a movement distance of the microneedle device system is adjusted. In this manner, it is possible to easily adjust the application amount of the microneedle device (area of the microneedle device applied to the skin).

Third Embodiment

Figure 25:
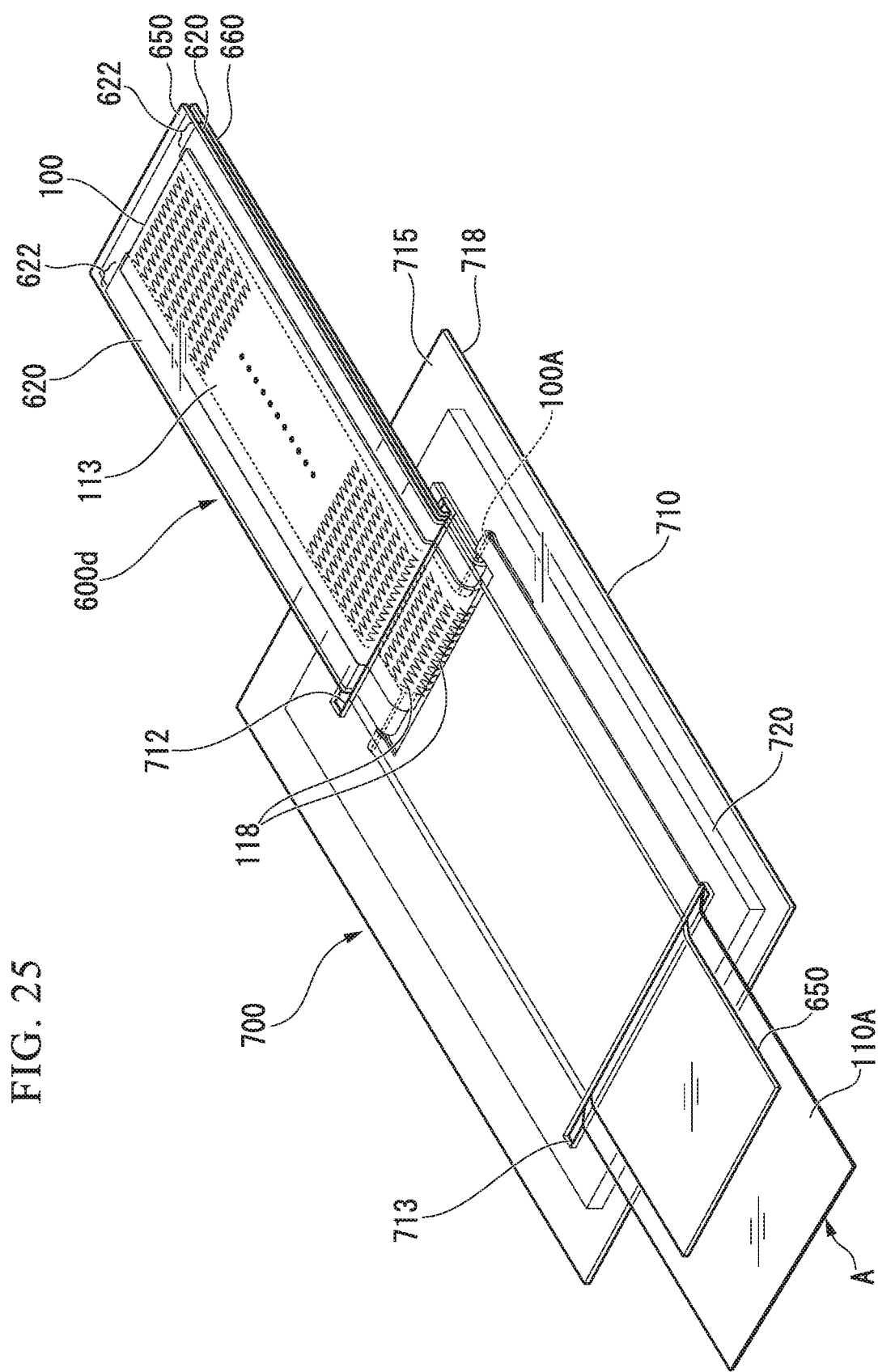
FIG. 25 is a perspective view illustrating an embodiment of the microneedle device system.

FIG. 25 is a perspective view illustrating an embodiment of the microneedle device system. The microneedle device system according to the present embodiment further includes a member A in the microneedle device system according to the above-described first embodiment.

Figure 26:
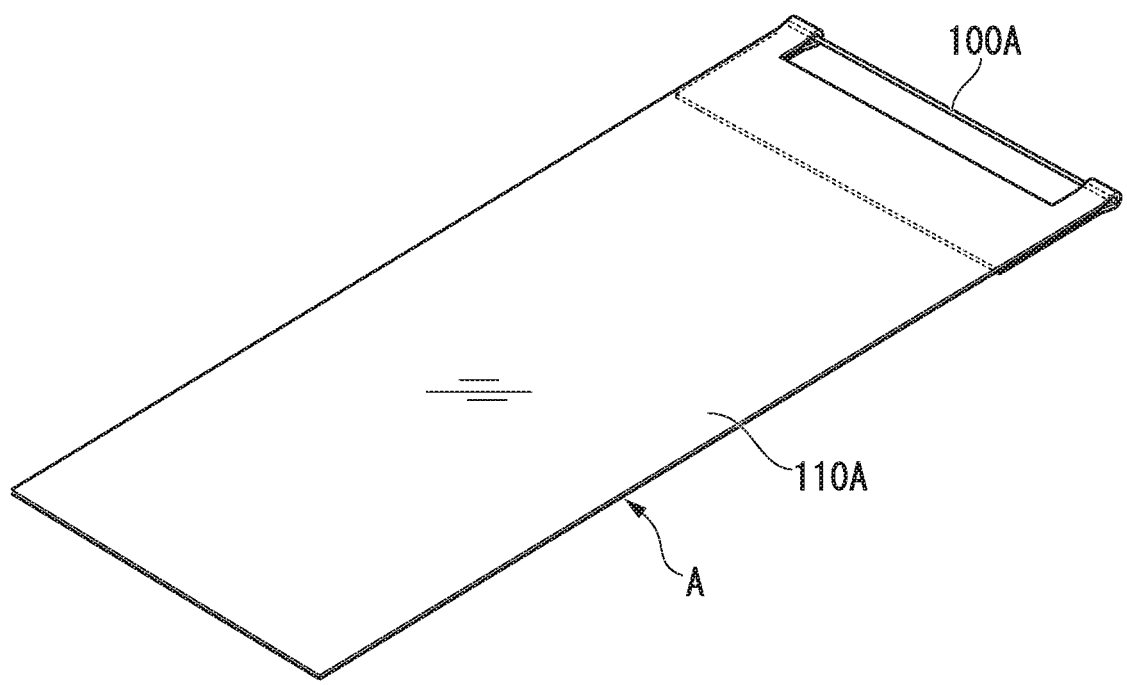
FIG. 26 is a perspective view illustrating a structure of a member A.

FIG. 26 is a perspective view illustrating a structure of the member A. The member A includes a cylindrical portion 100A and a support portion 110A for supporting both ends of the cylindrical portion 100A.

As illustrated in FIG. 25, the member A is disposed so that the cylindrical portion 100A is in contact with the ear surface 115 side of the sheet-like microneedle 100 in a portion where the microneedle device is bent. An end portion on a side opposite to the cylindrical portion 100A in the support portion 110A is caused to pass from the surface 718 side of the through-hole 713 of the auxiliary tool 700 toward the surface 715 side.

Figure 27A:
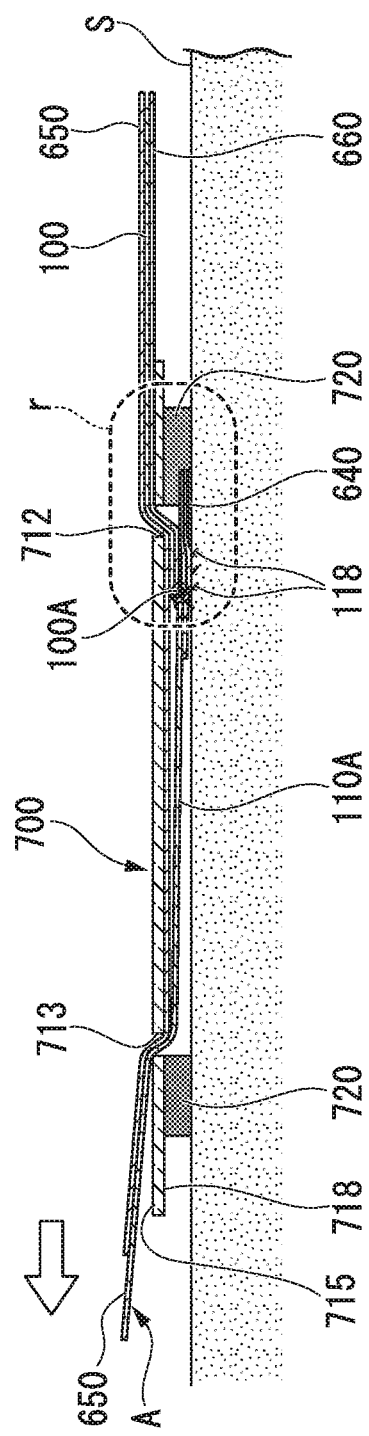
FIG. 27A is a sectional view illustrating an embodiment of the microneedle device system fixed onto the skin.
Figure 27B:
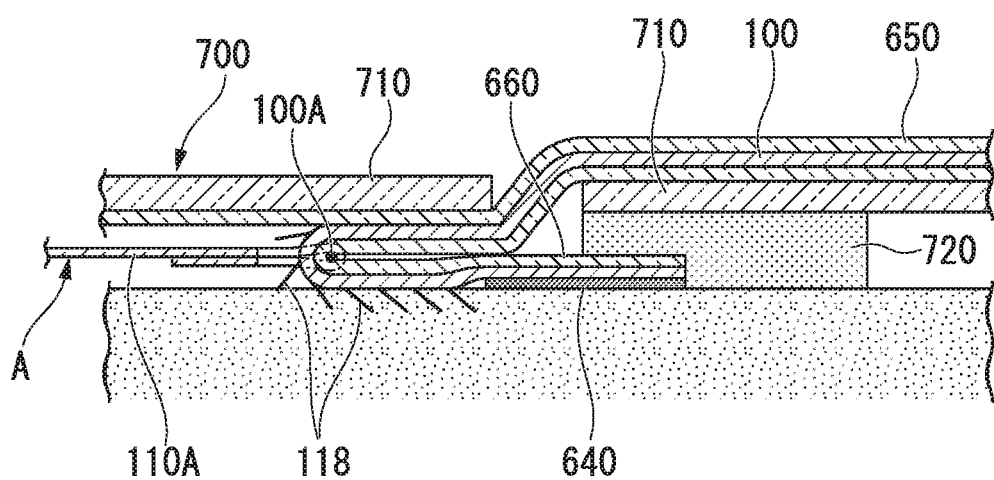
FIG. 27B is an enlarged view of a region r in FIG. 27A.

FIG. 27A is a sectional view illustrating a state where the microneedle device system according to the present embodiment is fixed onto the skin S. FIG. 27A illustrates a sectional view in the longitudinal direction of the auxiliary tool 700. FIG. 27B is an enlarged view of the region r in FIG. 27A. As illustrated in FIG. 27A, the auxiliary tool 700 is fixed onto the skin S by the adhesive layer 720. The sheet-like microneedle 100 is caused to pass through the through-hole 712 from the surface 715 side toward the surface 718 side, and is bent in the thickness direction on the skin S. In addition, the cylindrical portion 100A of the member A is disposed while being in contact with a bent portion of the microneedle device.

Here, a portion on the through-hole 713 side from the through-hole 712 in the substrate 710 functions as a bending portion for bending the microneedle device 600d in the thickness direction. In addition, the cylindrical portion 100A of the member A also functions as the bending portion for bending the microneedle device 600d in the thickness direction.

A user pinches one end of the support portion 110A of the member A, and pulls one end in a direction indicated by an arrow FIG. 27A, that is, in a direction away from one end fixed by the through-hole 712 and the adhesive layer 640. Through this operation, the sheet-like microneedle 100 is guided by the liner 650, passes through the through-hole 712, and enters a space between the skin S and the substrate 710 of the auxiliary tool 700.

The sheet-like microneedle 100 is bent 180 degrees inside this space. Similarly to a case of the microneedle device system according to the above-described first embodiment, the microneedle 118 located in the bent portion is raised from the skin contact surface 113, and the raised microneedle 118 pierces the skin S.

<Application of Microneedle Device to Skin>

The microneedle device can also be applied to the skin without using the auxiliary tool as described below.

Figure 19:
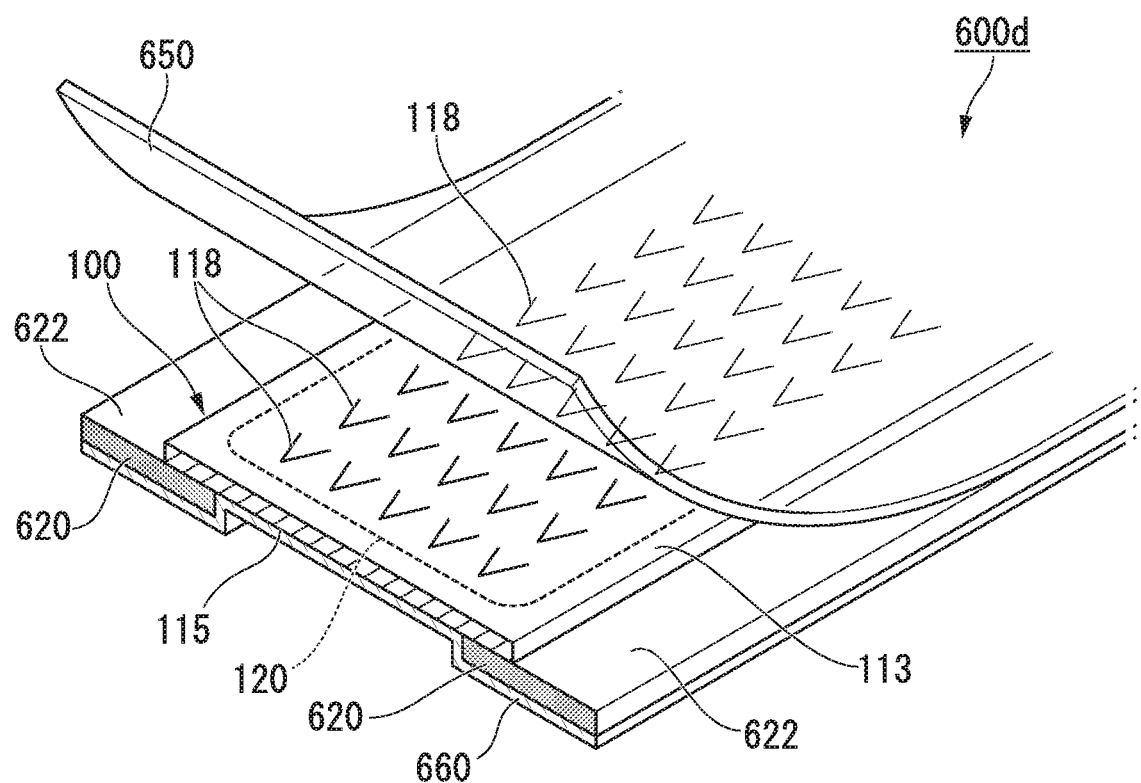
FIG. 19 is a perspective view illustrating a structure of a microneedle device according to an embodiment.
Figure 20:
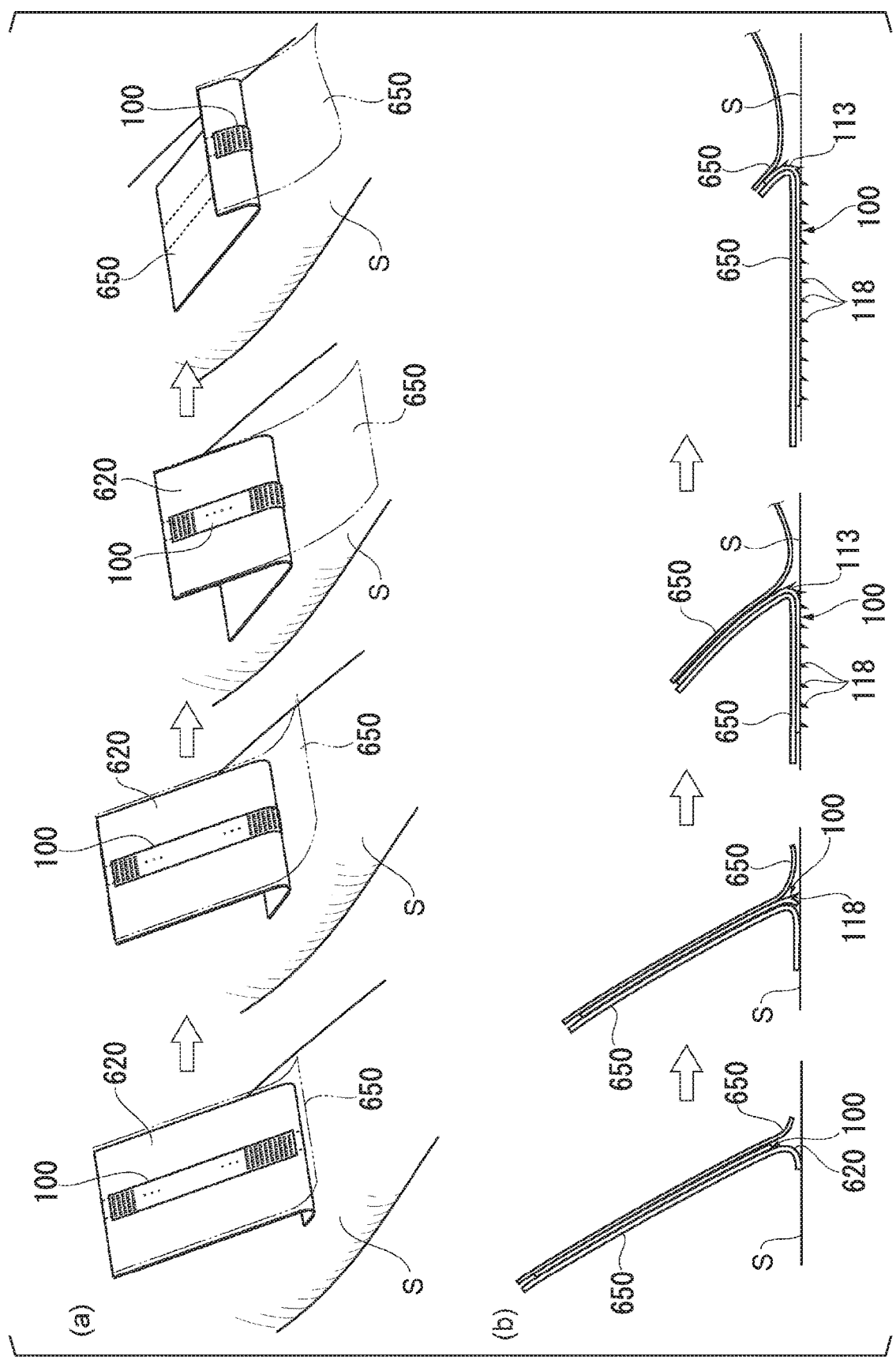
FIGS. 20(a) and 20(b) are views describing a use example of a microneedle device.

The microneedle device 600d according to the above-described fourth embodiment will be described as an example. FIG. 19 is a perspective view illustrating a structure of the microneedle device 600d. FIG. 20(a) is a schematic view describing a stepwise state where the microneedle device 600d is applied. FIG. 20(b) illustrates a sectional view in the longitudinal direction of the sheet-like microneedle 100 in each step of FIG. 20(a).

First, the user releases one end of the liner 650 on the skin contact surface 113 side, exposes a portion of the region 622 of the adhesive layer 620, and affixes this exposed portion to the skin S. Subsequently, while the user slowly releases the liner 650 on the skin contact surface 113 side so that the sheet-like microneedle 100 is bent at an acute angle, the region 622 of the adhesive layer 620 having the sheet-like microneedle 100 fixed thereto is affixed to the skin S.

Then, the microneedles 118 located in the bent portion of the sheet-like microneedle 100 are raised one row by one row from the skin contact surface 113 of the sheet-like microneedle 100, and the raised microneedles 118 pierce the skin S one after another.

According to the present embodiment, the user can also administer a desired amount of the drug by adjusting an application area of the sheet-like microneedle 100. In the microneedle device 600d, the adhesive layer is not laminated on the skin piercing region 120 of the rear surface 115 of the sheet-like microneedle 100. Therefore, when the sheet-like microneedle 100 is bent in the thickness direction, a raised state of the microneedle 118 is satisfactory, and the sheet-like microneedle 100 can efficiently pierce the skin. In addition, the region 622 of the adhesive layer 620 enables the microneedle device 600d to be fixed onto the skin S. In addition, in a case where the adhesive layer 620 contains a drug, the drug can be efficiently administered to a living body via the skin pierced by the microneedle 118.

EXAMPLE

Next, the present invention will be described in more detail with reference to examples. However, the present invention is not limited to the following examples.

Example 1

A triangular microneedle is formed on a sheet made of stainless steel having a thickness of 5 μm with an arrangement illustrated in FIG. 1 so as to obtain a sheet-like microneedle. The length of each microneedle is set to 500 μm, and the angle of the distal end of the microneedle is set to 45°. An adhesive layer is laminated so as to protrude from the sheet-like microneedle on a portion excluding the skin piercing region of the rear surface of the sheet-like microneedle. Subsequently, each liner is attached to the skin contact surface side of the sheet-like microneedle and the outer surface side of the rear surface side. A microneedle device system as illustrated in FIG. 15 is prepared, thereby configuring a microneedle device system according to Example 1.

Example 2

A microneedle device system according to Example 2 is obtained in the same manner as that Example 1, except that the sheet made of stainless steel having the thickness of 10 μm is used.

Example 3

A microneedle device system according to Example 3 is obtained in the same manner as that in Example 2, except that an angle of the distal end of the microneedle is set to 25 degrees.

EVALUATION OF RAISED STATE OF MICRONEEDLE

A transparent acrylic plate instead of the skin S in FIG. 16A is used. The microneedle device system according to Examples 1 to 3 is applied to the acrylic plate in the same manner as that in FIG. 16A so as to observe a state where the microneedle is raised.

More specifically, first, the adhesive layer of the auxiliary tool is affixed to the transparent acrylic plate. Subsequently, while the end of the liner having the sheet-like microneedle attached thereto is pinched and pulled in the direction indicated by the arrow in FIG. 16A, the folded and exposed adhesive layer is affixed to the acrylic plate. A raised state of the microneedle is evaluated in a direction opposite to the acrylic plate.

As a result, it is confirmed that the microneedle is also satisfactorily raised in the microneedle device systems according to any one of Examples 1 to 3.

INDUSTRIAL APPLICABILITY

According to the present invention, it is possible to provide a microneedle device system which includes a sheet-like microneedle so as to improve a raised state of a microneedle.

REFERENCE SIGNS LIST

100 Sheet-like microneedle
110 sheet
113 Skin contact surface
115 Rear surface
118 Microneedle
120 Skin piercing region
600a, 600b, 600c, 600d, 600e, 600f, 600g, 600h, 600i, 600a', 600b', 600c', 600d', 600e', 600f', 600h', 600i' Microneedle device
610, 620, 630, 640, 720 Adhesive layer
622, r Region
623, 633 Surface
650 Liner
660 Support
700, 1500 Auxiliary tool
710 Substrate
712, 713 Through-hole
715, 718 Surface
1510 Housing
1520 Microneedle device attachment portion
1550 Bending portion
1530 Liner-winding portion
1540, 1560 Guide
F1, F2, F3, F4 Force
D Distance
S Skin
P Bending point
A Member
100A Cylindrical portion
110A Support portion

The invention claimed is:

1. A microneedle device system, comprising:
   a microneedle device having
      a sheet-like microneedle having a sheet in which one surface is a skin contact surface and the other surface is a rear surface, one portion of the sheet-like microneedle being a skin piercing region, in which a plurality of microneedles are formed substantially along a surface of the sheet, whereby the plurality of microneedles are disposed in a first position in alignment in a longitudinal direction and a width direction of the sheet with distal ends of the plurality of microneedles facing one end of the sheet, and in which the distal ends of the of microneedles in the skin piercing region are movable from the first position to a second position whereby the distal ends of the plurality of microneedles are raised from the skin contact surface so as to be capable of piercing skin when the sheet is bent in a thickness direction,
   an adhesive layer that is disposed on a site excluding the skin contact surface of the skin piercing region of the sheet, and
   a liner that is attached to the adhesive layer so as to be releasable therefrom; and
   an auxiliary tool which has a bending portion for bending the microneedle device in the thickness direction, and on which the microneedle device is mounted so as to be movable along the bending portion.

2. The microneedle device system according to claim 1, wherein the adhesive layer is disposed on a site excluding the rear surface of the skin piercing region of the sheet.

* * * * *